(12) United States Patent
Ziegenbalg et al.

(10) Patent No.: US 11,318,732 B2
(45) Date of Patent: *May 3, 2022

(54) MACHINE ARRANGEMENT FOR SEQUENTIAL PROCESSING OF SHEET-TYPE SUBSTRATES

(71) Applicant: KOENIG & BAUER AG, Würzburg (DE)

(72) Inventors: Christian Ziegenbalg, Weinböhla (DE); Uwe Becker, Radebeul (DE); Ulrich Köhler, Radebeul (DE); Frank Schumann, Moritzburg / Friedewald (DE); Carsten Reinsch, Radebeul (DE); Michael Koch, Dresden-Cossebaude (DE)

(73) Assignee: KOENIG & BAUER AG, Wurzburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/158,165

(22) Filed: Jan. 26, 2021

(65) Prior Publication Data

US 2021/0146679 A1 May 20, 2021

Related U.S. Application Data

(63) Continuation of application No. 16/868,568, filed on May 7, 2020, now Pat. No. 10,933,627, which is a
(Continued)

(30) Foreign Application Priority Data

Sep. 9, 2015 (DE) ..................... 10 2015 217 229.5
Apr. 29, 2016 (WO) ................. PCT/EP2016/059647

(51) Int. Cl.
*B41F 19/00* (2006.01)
*B41F 23/04* (2006.01)
(Continued)

(52) U.S. Cl.
CPC ............ *B41F 19/001* (2013.01); *A61B 3/005* (2013.01); *A61B 3/0025* (2013.01); *A61B 3/04* (2013.01);
(Continued)

(58) Field of Classification Search
CPC .... B41F 19/001; B41F 19/007; B41F 19/008; B41F 21/05; B41F 23/0453;
(Continued)

(56) References Cited

U.S. PATENT DOCUMENTS 5,555,805 A   9/1996  Lapp
5,983,793 A   11/1999 Volz et al.
(Continued)

FOREIGN PATENT DOCUMENTS

DE       243 007 A1    2/1987
DE       10156800 B4   7/2002
(Continued)

OTHER PUBLICATIONS

International Search Report of PCT/EP2016/069067 dated Apr. 19, 2017.
(Continued)

*Primary Examiner* — David H Banh
(74) *Attorney, Agent, or Firm* — Mattingly & Malur, PC

(57) ABSTRACT

A machine arrangement, for sequentially processing sheet-type substrates, includes a plurality of different processing stations, one of which includes a non-impact printing device that prints the substrates. The processing station, including the non-impact printing device, also includes a printing cylinder, on the circumference of which, the non-impact printing device that prints the substrates is arranged. On the circumferential surface of the printing cylinder, four substrates are or can be placed behind each other in the circumferential direction. Each of the substrates that are to
(Continued)

be conveyed are retained in one of a force-locking and a form-fitting manner on the circumferential surface of the printing cylinder by at least one retaining element.

20 Claims, 15 Drawing Sheets

Related U.S. Application Data continuation of application No. 16/551,863, filed on Aug. 27, 2019, now Pat. No. 10,682,850, which is a continuation of application No. 15/757,986, filed as application No. PCT/EP2016/069067 on Aug. 10, 2016, now Pat. No. 10,538,077.

(51) Int. Cl.

| | | |
|---|---|---|
| B41J 3/54 | (2006.01) | |
| B41J 3/60 | (2006.01) | |
| B41J 11/00 | (2006.01) | |
| B41F 25/00 | (2006.01) | |
| B41F 21/05 | (2006.01) | |
| A61B 3/00 | (2006.01) | |
| A61B 3/04 | (2006.01) | |
| A61B 3/103 | (2006.01) | |
| A61B 3/14 | (2006.01) | |

(52) U.S. Cl.
CPC ............... *A61B 3/103* (2013.01); *A61B 3/14* (2013.01); *B41F 19/007* (2013.01); *B41F 19/008* (2013.01); *B41F 21/05* (2013.01); *B41F 23/0453* (2013.01); *B41F 23/0456* (2013.01); *B41F 23/0466* (2013.01); *B41F 25/00* (2013.01); *B41J 3/546* (2013.01); *B41J 3/60* (2013.01); *B41J 11/0015* (2013.01); *B41J 11/0022* (2021.01); *B41J 11/00214* (2021.01); *B41J 11/00216* (2021.01); *B41P 2217/11* (2013.01)

(58) Field of Classification Search
CPC .. B41F 23/0456; B41F 23/0466; B41F 25/00; B41F 3/546; B41F 3/60; B41F 11/02; B41J 3/546; B41J 3/60; B41J 11/0015; B41J 11/002; B41P 2217/11; A61B 3/04; A61B 3/103; A61B 3/14; A61B 3/005
See application file for complete search history.

(56) References Cited

U.S. PATENT DOCUMENTS

| | | | |
|---|---|---|---|
| 6,363,234 B2 | 3/2002 | Landa et al. | |
| 6,612,569 B2 | 9/2003 | Schaum | |
| 6,718,908 B1 | 4/2004 | Bayer | |
| 7,909,454 B2 | 3/2011 | Koto et al. | |
| 9,422,126 B2 | 8/2016 | Kondo et al. | |
| 9,427,986 B2 | 8/2016 | Furukawa | |
| 9,579,879 B2 | 2/2017 | Raksha | |
| 9,718,286 B2 | 8/2017 | Dolz et al. | |
| 10,259,211 B2 * | 4/2019 | Ziegenbalg | B41J 3/546 |
| 10,792,910 B2 * | 10/2020 | Ziegenbalg | B41F 19/007 |
| 2006/0065144 A1 | 3/2006 | DeMoore | |
| 2006/0208412 A1 | 9/2006 | Reinhard | |
| 2008/0098910 A1 * | 5/2008 | Koto | B41J 13/223 |
| | | | 101/118 |
| 2008/0236421 A1 | 10/2008 | Ito | |
| 2009/0079784 A1 | 3/2009 | Chiwata | |
| 2009/0178582 A1 * | 7/2009 | Dal Pont | B41F 23/08 |
| | | | 101/126 |
| 2009/0241787 A1 | 10/2009 | DiGenova | |
| 2009/0244237 A1 | 10/2009 | Kachi | |
| 2009/0284561 A1 | 11/2009 | Fukui | |
| 2009/0291215 A1 | 11/2009 | Makuta | |
| 2009/0311426 A1 * | 12/2009 | Nakazawa | B41J 13/223 |
| | | | 427/256 |
| 2011/0205321 A1 | 8/2011 | Kobayashi et al. | |
| 2012/0128395 A1 | 5/2012 | Izawa | |
| 2013/0021402 A1 | 1/2013 | Tsuzawa | |
| 2013/0222500 A1 | 8/2013 | Chiwata | |
| 2013/0300057 A1 | 11/2013 | Kondo | |
| 2014/0331877 A1 * | 11/2014 | Kamoda | B41F 19/007 |
| | | | 101/212 |
| 2015/0246556 A1 | 9/2015 | Houjou | |

FOREIGN PATENT DOCUMENTS

| | | |
|---|---|---|
| DE | 10312870 A1 | 2/2004 |
| DE | 102004002132 A1 | 8/2005 |
| DE | 102005021186 A1 | 11/2005 |
| DE | 102009000513 A1 | 8/2010 |
| DE | 102009000518 A1 | 8/2010 |
| DE | 102009000521 A1 | 8/2010 |
| DE | 102012200650 A1 | 8/2012 |
| DE | 102012218840 A1 | 5/2013 |
| DE | 102013209908 A1 | 12/2013 |
| DE | 102013215277 A1 | 3/2014 |
| DE | 102013019814 A1 | 6/2014 |
| DE | 102013211250 A1 | 12/2014 |
| DE | 102014010904 B3 | 1/2015 |
| DE | 102015211440 B3 | 4/2016 |
| DE | 102016207398 B3 | 8/2016 |
| EP | 0 620 115 A1 | 10/1994 |
| EP | 1 818 177 A2 | 8/2007 |
| EP | 2540513 A1 | 1/2013 |
| EP | 2657025 A1 | 10/2013 |
| EP | 2 889 242 A1 | 7/2015 |
| GB | 2511606 A | 9/2014 |
| JP | 2011-161840 A | 8/2011 |
| JP | 2014-210438 A | 11/2014 |
| JP | 2015-044345 A | 3/2015 |
| JP | 2015-063398 A | 4/2015 |
| WO | 2004/013704 A1 | 2/2004 |
| WO | 2006/043269 A2 | 4/2006 |
| WO | 2010/086203 A1 | 8/2010 |
| WO | 2010/086205 A1 | 8/2010 |
| WO | 2013/178675 A1 | 12/2013 |

OTHER PUBLICATIONS

Jul. 23, 2019 Office Action issued in Japanese Patent Application No. 2018-512547.
https://www.youtube.com/watch?v=inpV5gcVCcM; published on Jun. 6, 2012.
Helmut Teschner "Offsetdrucktechnik", 6. vollig neu bearbeitete Auflage 1989, ISBN, pp. 331-336.

* cited by examiner

MACHINE ARRANGEMENT FOR SEQUENTIAL PROCESSING OF SHEET-TYPE SUBSTRATES

CROSS-REFERENCE TO RELATED APPLICATIONS

This application is a continuation of U.S. patent application Ser. No. 16/868,568, filed May 7, 2020, which is a continuation of U.S. patent application Ser. No. 16/551,863 filed Aug. 27, 2019, now U.S. Pat. No. 10,682,850, which is a continuation application of U.S. patent application Ser. No. 15/757,986, filed Mar. 7, 2018, now U.S. Pat. No. 10,538,077, which is the U.S. National Phase, under 35 U.S.C. § 371, of PCT/EP2016/069067, filed Aug. 10, 2016; published as WO2017/041982A2 and A3 on Mar. 16, 2017 and claiming priority to DE 10 2015 217 229.5, filed Sep. 9, 2015 and to PCT/EP2016/059647, filed Apr. 29, 2016, the disclosures of which are expressly incorporated herein in their entireties by reference.

FIELD OF THE INVENTION

The present invention relates to a machine arrangement for the sequential processing of sheet-type substrates. The machine arrangement includes a plurality of different processing stations. One of these processing stations includes a non-impact printing unit that prints each of the substrates. The processing station that includes the non-impact printing unit also includes a printing cylinder. The non-impact printing unit is arranged on the periphery of the printing cylinder which is embodied as a quadruple-sized printing cylinder. A transfer drum that is double-sized or triple-sized is disposed directly upstream of the printing cylinder. Alternatively, a transfer cylinder which is embodied as a triple sized transfer cylinder is disposed directly downstream of the printing cylinder.

BACKGROUND OF THE INVENTION

WO 2004/013704 A1 describes a digital printing machine for direct non-contact sheet-fed printing having a digital printing couple that is unformatted in the circumferential direction, and having a transport apparatus downstream from the digital printing couple, wherein the transport apparatus has grippers for holding sheets on its periphery, the transport apparatus preferably having a plurality of transport cylinders and/or transport belts and/or impression cylinders.

EP 2 540 513 A1 describes a machine arrangement for the sequential processing of a plurality of sheet-type substrates, each having a front side and a back side, said machine arrangement comprising a first printing cylinder and a second printing cylinder, wherein at least one first non-impact printing unit, which prints the front side of the substrate in question, and a dryer, which dries the front side of the substrate in question that has been printed by the first non-impact printing unit, are arranged downstream from the first non-impact printing unit in the direction of rotation of the first printing cylinder, each on the periphery of the first printing cylinder, wherein at least one second non-impact printing unit, which prints the back side of the substrate in question, and a dryer, which dries the back side of the substrate in question that has been printed by the second non-impact printing unit, are arranged downstream from the second non-impact printing unit in the direction of rotation of the second printing cylinder, each on the periphery of the second printing cylinder, wherein the first printing cylinder and the second printing cylinder are arranged such that they form a common roller nip, wherein in this common roller nip, the first printing cylinder transfers the substrate in question, which has been printed on the front side and dried, directly to the second printing cylinder.

DE 103 12 870 A1 describes a digital printing machine for sheet-fed printing, having a digital printing couple that is format-free in the circumferential direction, an intermediate cylinder downstream from the digital printing couple, coated at least partially with an elastic material, and an impression cylinder downstream from the intermediate cylinder, wherein the impression cylinder has sheet-retaining grippers and the intermediate cylinder has recesses on its periphery for accommodating the grippers.

DE 101 56 800 B4 discloses a printing couple comprising a transport device embodied as rotational for transporting a printing stock sheet, which is embodied with a retaining device for retaining the printing stock sheet, and comprises an NIP (non-impact printing) print head aligned with the transport device for printing the printing stock sheet, wherein the retaining device is mounted to be periodically displaceable into the interior of the transport device.

DE 10 2015 211 440 B3 which was published subsequently discloses a sheet transport drum of a sheet processing machine having at least two sheet supporting surfaces with suction openings, wherein each sheet supporting surface is formed from a first and a second comb segment having segment prongs, wherein suction grooves are provided in the segment prongs and an undercut suction groove is provided in the sheet supporting surface of a respective second comb segment, and also having a rotary valve for cycled exposure to suction air, wherein a plurality of vacuum sources is provided, and each undercut suction groove is associated with a vacuum source via the rotary valve.

U.S. Pat. No. 6,363,234 B2 discloses a digital printing machine having a quadruple-sized printing cylinder.

U.S. Pat. No. 7,909,454 B2 discloses a digital printing machine having a printing cylinder on whose circumferential surface four printing sheets, each held by a retaining means, can be arranged in the circumferential direction, wherein the printing sheets are transferred from a single-sized transfer cylinder to the printing cylinder.

DE 10 2013 211 250 A1 discloses a printing machine having a plurality of printing couples that jointly print a printing stock, wherein at least two of these printing couples are arranged one behind the other in a row along a transport path provided for the printing stock, wherein at least one of these printing couples arranged in a row is embodied as an inkjet system, wherein the inkjet system in question is embodied such that this inkjet system prints varying or at least variable information on a target surface provided on the printing stock in an ongoing printing process, wherein at least one mark applied to the printing stock is present, wherein a detection device for detecting the at least one mark applied to the printing stock is provided, wherein an adjusting device that adjusts the position of the inkjet system in question at least transversely to the transport path provided for the printing stock is provided between the inkjet system in question and one of the printing couples arranged in a row for this inkjet system, wherein the current position of the inkjet system in question is or at least can be adjusted by positioning the inkjet system in question by means of the adjusting device on the basis of the at least one mark detected by the detection device in the ongoing printing process, relative to the position of the target surface that is provided for printing the varying or at least variable information in the ongoing printing process.

DE 10 2012 218 840 A1 describes a method for transferring a transfer film that is releasable from an imaging transfer layer to a printing sheet provided with an adhesive coating by means of a coating unit, wherein the coating unit comprises an impression cylinder and a pressing roller that form a common transfer nip, by means of which the transfer film can be guided from a film supply roll, touching the pressing roller, such that it comes to rest with the transfer layer on the printed sheet guided on the impression cylinder, and is guided under pressure, together with the printed sheet, through the transfer nip for transferring the coating, a) wherein in the application unit, adhesive is applied in the form of the image to the printed sheet, b) wherein in the transfer nip, a subject of the transfer layer is transferred with pressing from the transfer film to the printed sheet provided with an adhesive image, c) wherein a protective layer is applied at least to the transfer layer applied to the printed sheet in this way, d) wherein, after application of the protective layer, the protective layer is dried on the printed sheet, and e) wherein after drying of the protective layer, the printed sheet is overprinted with images over all or part of its extension, including the transfer layer and the protective layer.

DE 10 2014 010 904 B3 describes an apparatus for two-sided printing of sheet-type printing stock, wherein the printing stock is guided around more than 360° on an impression cylinder, wherein the active region of an ink application unit, which has already printed the front side of the printing stock on an impression cylinder upstream, is re-entered by the printing stock, this time with its back side facing the ink application unit, wherein the ink application unit can preferably be pivoted between two impression cylinders disposed downstream from one another, and wherein the pivotable ink application unit is an inkjet print head, for example.

DE 10 2009 000 518 A1 describes a sheet-fed printing machine having a feed unit for loading printing sheets to be printed into the sheet-fed printing machine, and having at least one printing couple and/or coating unit for printing the printing sheets with a static print image that is identical for all printing sheets, and having a delivery unit for discharging printed sheets from the sheet-fed printing machine, and having at least one printing forme-free printing unit integrated into the sheet-fed printing machine for printing the printing sheet with a dynamic, variable print image in particular, wherein the/each printing forme-free printing unit is integrated into the sheet-fed printing machine, where it can be controlled as a function of the process parameters or operating parameters or order parameters or quality parameters.

SUMMARY OF THE INVENTION

The object of the present invention is to create a machine arrangement for the sequential processing of sheet-type substrates.

The object is achieved according to the invention by the provision of four substrates that are to be printed by the non-impact printing unit. These are, or at least can be, arranged one behind the other in a circumferential direction of the circumferential surface of the printing cylinder. Each of these four substrates to be transported is held in one of a form-locking and a form-fitting manner on the circumferential surface of the printing cylinder by the use of at least one retaining element. The quadruple-sized printing cylinder may receive the substrates to be printed from the transfer drum which is located immediately upstream. Alternatively, the quadruple-sized printing cylinder transfers the printed substrates to the triple-sized transfer drum that is located immediately downstream of the printing cylinder.

The advantages achieved with the invention will be clear from the following descriptions.

The approach described here can be used in a hybrid machine arrangement for processing sheet-type substrates, preferably in a hybrid printing machine that variably utilizes the high productivity of a conventional printing unit that prints, for example, by an offset printing method or by a flexographic printing method or by a screen printing method, or a coating unit, in particular a coating unit, in combination with at least one non-impact printing unit embodied as an inkjet printer, for example, that prints variable printed images in a flexible manner, wherein the conventional printing unit or coating unit and the non-impact printing unit are each used in an ongoing inline production process, each at its optimum working speed. Such a hybrid machine arrangement is very advantageous in particular for the production of packaging means, for example, sheets for the production of folding boxes, because the strengths of each one of the printing units can be utilized, resulting in a flexible and economical production of the packaging means. Transporting sheet-type substrates by means of rotating bodies, in particular cylinders and gripper bars or gripper carriages, each of which transfers the sheet-type substrates in a gripper closure to a next following processing station, as is known from sheet-fed offset printing machines, ensures the highest possible register accuracy.

BRIEF DESCRIPTION OF THE DRAWINGS

Exemplary embodiments of the invention are illustrated in the drawings and described in greater detail below.

DESCRIPTION OF THE PREFERRED EMBODIMENTS

Figure 1:
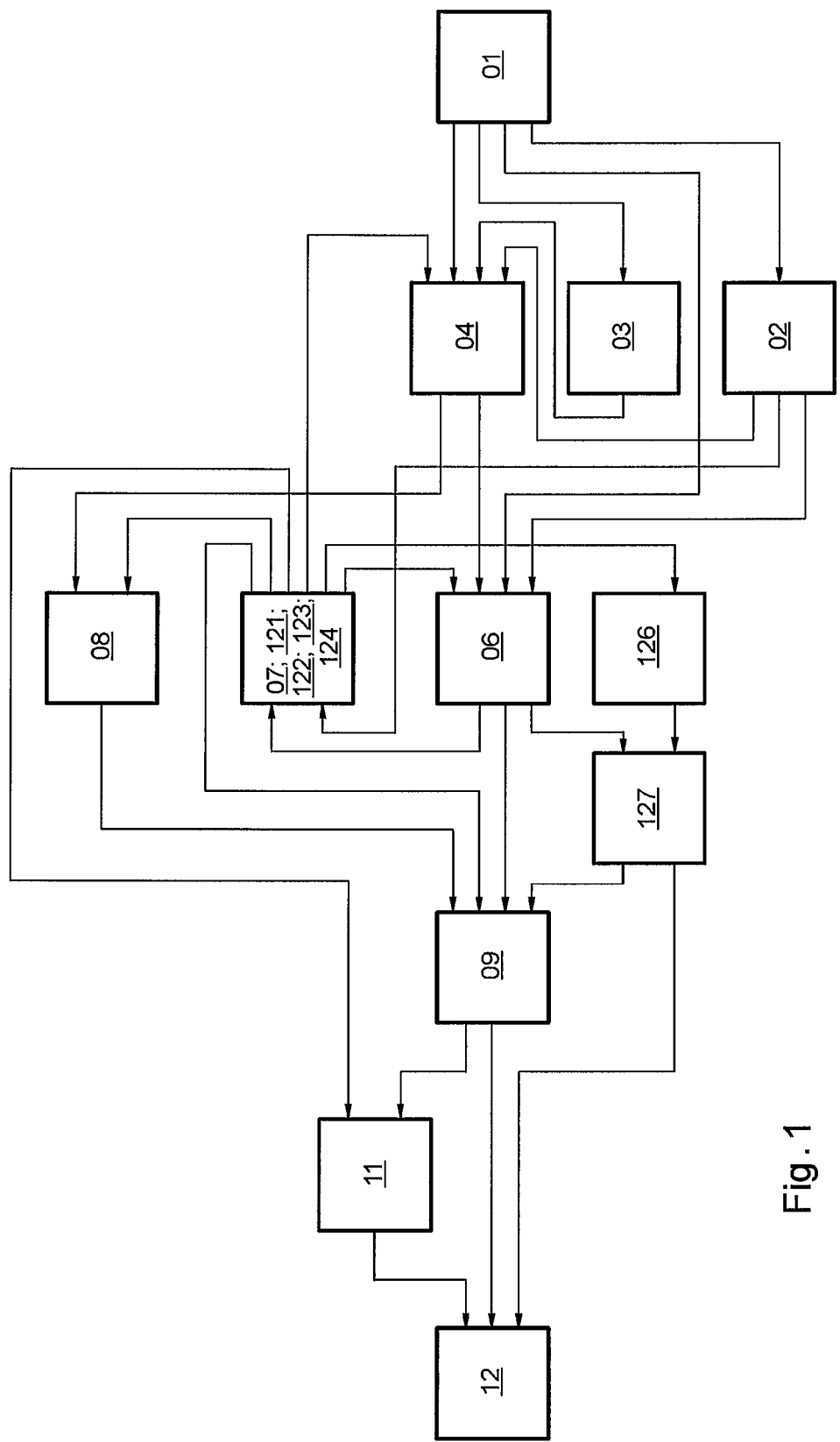
FIG. 1 shows a block diagram to illustrate the various production lines.

FIG. 1 is a block diagram illustrating various production lines, each being implementable with a machine arrangement having a plurality of different processing stations 01; 02; 03; 04; 06; 07; 08; 09; 11; 12, in particular, for processing at least one sheet-type substrate, in particular a printing stock, preferably a printing sheet, which is rectangular in particular, or more simply a sheet, wherein this at least one substrate is embodied as rigid or flexible, depending on the material, the thickness of the material and/or the base weight. Each of these processing stations 01; 02; 03; 04; 06; 07; 08; 09; 11; 12 is preferably embodied as an independently functional module, for example, wherein a module should be understood to be a machine unit or functional subassembly that is typically manufactured separately or at least is installed separately in its own frame. Each of processing stations 01; 02; 03; 04; 06; 07; 08; 09; 11; 12 disposed in the respective machine arrangement is thus preferably manufactured separately, and in a preferred embodiment can be tested individually in terms of its function, for example. Each machine arrangement, which is formed by selecting and assembling at least three different sheet processing stations 01; 02; 03; 04; 06; 07; 08; 09; 11; 12 that cooperate in a specific production process, embodies a specific production line. Each of the production lines shown, embodied as a certain machine arrangement having a plurality of processing stations 01; 02; 03; 04; 06; 07; 08; 09; 11; 12, is configured in particular for the production of a packaging means formed from the printing stock, preferably from the printed sheet. Each of the packaging means to be produced is, e.g. a folding box, which is produced from printed sheets. The various production lines are therefore configured in particular for producing different packaging means. The processing of the printing stock that is required during a specific production process is carried out inline, i.e., the processing stations 01; 02; 03; 04; 06; 07; 08; 09; 11; 12 that are involved in a specific production process are used one after another in an ordered sequence and in coordination with one another as the printing stock passes through the machine arrangement selected for said production process and comprising the respective processing stations 01; 02; 03; 04; 06; 07; 08; 09; 11; 12, without providing intermediate storage for the printing stock, i.e., the processed sheets, during the production process carried out by said machine arrangement.

All of the production lines shown in FIG. 1 have in common the fact that they each cooperate with a processing station 06 comprising at least one non-impact printing unit 06, preferably a plurality of non-impact printing units 06, for example, four, five, six or seven, each in particular individually controlled, wherein these non-impact printing units 06 are preferably arranged one behind the other in transport direction T of the printing stock and are embodied to be able to print the printing stock at least nearly over its entire width transversely to transport direction T. A non-impact printing unit 06 uses a printing method without a fixed printing forme and can in principle print the printing stock, e.g. a sheet that has just been supplied to said printing unit 06, with a print image that is different from the print image that preceded it, from one printing to the next. Each non-impact printing unit 06 is implemented in particular as at least one inkjet printer or as at least one laser printer. Inkjet printers are matrix printers, in which a print image is created by the targeted ejection or deflection of small ink droplets, such that the inkjet printer is embodied either as a device with a continuous ink jet (continuous ink jet=CIJ) or as a device that sprays individual ink droplets (drop on demand=DOD). Laser printers produce print images by an electrophotography method. Non-impact printing unit 06 is also referred to as a digital printing machine, for example.

In the following discussion, it is assumed by way of example that a sequence of flexurally rigid sheets, in particular, e.g. of a paper, a single-layer or multilayer paperboard or a cardboard, are processed in the respective machine arrangement by a plurality of processing stations 01; 02; 03; 04; 06; 07; 08; 09; 11; 12, in particular to produce a packaging means. Paper, paperboard and cardboard as printing stock differ in their respective base weight, i.e., the weight in grams for a square meter of this printing stock. In general, the aforementioned printing stock having a base weight between 7 $g/m^2$ and 150 $g/m^2$ is classified as paper, between 150 $g/m^2$ and 600 $g/m^2$ is paperboard and more than 600 $g/m^2$ is cardboard. Paperboard, which has good printability and is suitable for a subsequent finishing or processing such as coating and punching, is used in particular to produce folding boxes. In terms of pulp content, these types of cardboard may be, for example, wood-free, may have a low wood content or some wood content, or may contain recycled paper. In terms of construction, multilayer paperboards have a cover layer, an insert and a substrate as a back side. In terms of surface properties, paperboards may be uncoated, pigmented, coated or cast-coated, for example. The sheet format may range from 340 mm×480 mm to 740 mm×1060 mm, for example, with the first number in the format specification typically indicating the length in transport direction T of the sheets, and the second number representing the width of the sheet orthogonally to transport direction T.

In the block diagram in FIG. 1, each production line that can be represented with a plurality of processing stations 01; 02; 03; 04; 06; 07; 08; 09; 11; 12 runs substantially from right to left, with each of the directional arrows that connect two processing stations 01; 02; 03; 04; 06; 07; 08; 09; 11; 12 to one another indicating a transport path to be traveled by the printing stock and the associated transport direction T for traveling from one processing station 01; 02; 03; 04; 06; 07; 08; 09; 11; 12 to the next processing station 01; 02; 03; 04; 06; 07; 08; 09; 11; 12 selected in the machine arrangement intended for the respective production process. Each production process begins with sheets being provided in processing station 01, with processing station 01 being embodied as a feed unit 01, e.g. as a sheet feed unit 01 or as a magazine feed unit 01. A sheet feed unit 01 typically receives a pile of sheets stacked on a pallet, for example, whereas a magazine feed unit 01 comprises a plurality of compartments, into each of which sheets, in particular piles of different types of sheets or sheets of different formats, are or at least can be inserted. Feed unit 01 separates the stacked sheets for single feed, for example, by means of a suction head 41, and guides them in a sequence of separated sheets or in a shingled stream to the next processing station 02; 03; 04; 06 in the specific production process. The next processing station 02; 03; 04 is embodied, for example, as a paper application unit 02 or as a cold foil application unit 03 or as an offset printing unit 04 or as a flexographic printing unit 04. The next processing station 06 may also be, e.g. the at least one non-impact printing unit 06 directly. Offset printing unit 04 is preferably embodied as a sheet-fed offset printing machine, in particular as a sheet-fed printing machine having a plurality of printing couples 86 arranged based on the unit construction principle. Offset printing unit 04 provides the sheets with at least one static print image, i.e., a print image that does not vary during the printing process because it is bound to the printing forme used, whereas non-impact printing unit 06 provides the sheets with at least one print image that varies or is at least variable.

If the processing station 03 immediately following feed unit 01 is the cold foil application unit 03, then the sheet is typically transported from there to processing station 04, embodied as offset printing unit 04. In coil foil application unit 03, a metallized coating layer that is released from a carrier film is transferred to the printing stock. A wide variety of different metal effects can be achieved by overprinting this coating layer with an offset printing unit 04, for example. Cold foil application unit 03 is advantageously embodied as integrated into offset printing unit 04, for example, in that two additional printing couples 87; 88 are provided in offset printing unit 04. A special adhesive is applied to the printing stock, i.e., the sheet, by means of a standard printing forme in the first printing couple 87 in transport direction T of the printing stock. A second printing couple 88 in transport direction T of the printing stock is furnished with a film transfer device having the coating layer to be transferred. The film that carries the coating layer is guided from an unwinding station to a press nip between a transfer cylinder and a printing cylinder that cooperates with this transfer cylinder, and is thereby brought into contact with the printing stock. An aluminum layer and a protective coating layer, the coloring of which influences the color effect, provide coloring in the coating layer. By adhesion of an adhesive layer to the glue layer printed thereon, the transfer layers are left adhering to the substrate. The backing film is then wound up again. After the cold foil transfer, overprinting using conventional printing inks and UV inks and hybrid inks is possible inline, in particular in offset printing unit 04, in order to produce a variety of metallic color shades.

A printing stock, which is particularly absorbent, for example, and/or is to be prepared for printing in a non-impact printing unit 06, is supplied by feed unit 01 to the next processing station 02, embodied, for example, as a primer application unit 02 for coating at least one surface of the printing stock with a water-based primer, for example, in particular to seal the surface prior to printing or coating. Priming involves an undercoating or initial coating of the printing stock to improve or enable adhesion of an ink or printing ink to be applied thereafter to the printing stock. Primer application unit 02 is formed, for example, in combination with a printing couple 86 of a rotary printing machine and comprises, for example, a printing couple cylinder 82 that cooperates with an impression cylinder 119 and includes a forme roller 83, preferably in the form of an anilox roller 83, which is or at least can be thrown onto this printing couple cylinder 82, as well as at least one doctor blade 84, in particular an ink chamber blade system 84 extending in the axial direction of the forme roller 83 (FIGS. 3 through 5, 8, 9).

The primer is applied to the printing stock either over its full surface area or to only certain, i.e., previously defined, areas, i.e. partially, by means of primer application unit 02. The printing stock, e.g. sheets, processed in primer application unit 02, is fed, for example, to an offset printing unit 04 and/or a non-impact printing unit 06 as the next processing station.

The flexographic printing carried out by a processing station 04, embodied, e.g. as a flexographic printing unit 04, is a direct letterpress method, in which the raised areas of the printing forme are image-carrying areas, and which is frequently used for printing packaging materials made of paper, paperboard or cardboard, metallized film, or a plastic such as PE, PET, PVC, PS, PP, PC. In flexographic printing, low-viscosity printing inks and flexible printing plates made of photopolymer or rubber are used. In general, a flexographic printing unit 04 includes a) an anilox roller, by means of which the printing forme is inked, b) a printing cylinder, also known as a forme cylinder, to which the printing forme is attached, and c) an impression cylinder, which guides the printing stock.

Processing station 04, which is embodied as flexographic printing unit 04 or as offset printing unit 04 and prints each of the sheets with at least one static print image, preferably has a plurality of printing couples 86, e.g. at least four, wherein each printing couple 86 preferably prints with a different printing ink, so that the printing stock is printed in multiple colors, for example, in four-color printing, as it passes through flexographic printing unit 04 or offset printing unit 04. The color shades yellow, magenta, cyan and black in particular are used as the printing inks. In an alternative embodiment of printing unit 04 to the flexographic printing method or the offset printing method, the processing station 04 that prints the sheets with at least one static print image each is embodied as a printing unit 04 that prints by a screen printing method.

After the printing stock has been processed in at least one non-impact printing unit 06, this printing stock is sent to a processing station 07 embodied, for example, as an intermediate dryer 07, wherein this intermediate dryer 07 is embodied as a dryer that dries the printing stock in question by irradiation with infrared or ultraviolet radiation, with the type of radiation being dependent in particular on whether the ink or printing ink applied to the printing stock is water-based or UV curing. After intermediate drying, the printing stock is sent to a processing station 08 embodied as a coating unit 08, for example. Coating unit 08 applies a dispersion coating, for example, to the printing stock, dispersion coatings consisting essentially of water and binders (resins), with surfactants stabilizing these dispersions. A coating unit 08 that applies a dispersion coating to the printing stock consists either of an anilox roller, an ink chamber blade and a forme roller (comparable to a flexographic printing couple), or of a dipping roller and forme roller. Flat and/or partial coatings are applied by means of a printing forme, preferably based on photopolymerization, for example. Special coating plates made of rubber may also be used for full-surface coatings. Downstream of coating unit 08, a processing station 09 embodied, e.g. as a dryer 09 is arranged in the transport path of the printing stock, wherein this dryer 09 is embodied as a dryer that dries the printing stock in question by irradiation with infrared radiation or by hot air. If the machine arrangement in question has multiple dryers 07; 09 along the transport path of the printing stock, then the dryer with reference numeral 09 is preferably the last of these multiple dryers 07; 09 in transport direction T of the printing stock, wherein intermediate dryer(s) 07 and (final) dryer 09 are embodied identically or may also be embodied differently. If a printing stock that dries by ultraviolet radiation will be supplied to dryer 09, i.e., a printing stock on which an ink or printing ink that cures by UV radiation or a coating that cures by UV radiation, for example, a glossy coating, is applied, then this dryer 09 is equipped with a radiation source that generates ultraviolet radiation. More intense glossy effects and matte effects can be achieved with dispersion coatings as compared with the traditional oil printing coating. Special visual effects can be achieved with effect pigments in the coating. Primer application unit 02, cold foil application unit 03 and coating unit 08 can be combined under the umbrella term of coating unit 02; 03; 08.

After drying, the printing stock is sent to a processing station 11, for example, which carries out a mechanical further processing of the printing stock, for example, by punching, creasing and/or cutting parts, in particular separating copies from their attachment in the preferably printed sheet. Each of the aforementioned types of further processing is carried out in and/or by a processing unit 46. Mechanical further processing is preferably carried out in cooperation with a cylinder transporting the respective sheet. Afterward or directly from dryer 09, the printing stock is transferred to a delivery 12, which forms the last processing station 12 in each of the production lines formed by a specific arrangement of processing stations 01; 02; 03; 04; 06; 07; 08; 09; 11; 12, as illustrated in FIG. 1. The previously processed sheets are preferably stacked on a pallet, for example, in delivery 12.

As illustrated in FIGS. 2 through 8, the aforementioned sequence of processing stations 01; 02; 03; 04; 06; 07; 08; 09; 11; 12 included in the machine arrangement may be modified only by way of example and dependent upon the printed product to be produced in each case.

In the production lines illustrated in FIG. 1 by way of example and used in particular for the production of packaging means, each production line comprises a machine arrangement having a selection of the group of aforementioned processing stations 01; 02; 03; 04; 06; 07; 08; 09; 11; 12. The following production lines are or at least can be formed, for example:

1. Sheet feed unit 01; primer application unit 02; non-impact printing unit 06;
   intermediate dryer 07 with IR radiation source for dispersion coating; coating unit 08; dryer 09 with IR radiation source or hot air; delivery 12
2. Sheet feed unit 01; primer application unit 02; non-impact printing unit 06; dryer 09 with IR radiation source or hot air; delivery 12
3. Sheet feed unit 01; primer application unit 02; non-impact printing unit 06; intermediate dryer 07 with IR radiation source; coating unit 08 for dispersion coating and UV curing coating; dryer 09 with IR radiation source or hot air and with UV radiation source; delivery 12
4. Sheet feed unit 01; cold foil application unit 03; offset printing unit 04; non-impact printing unit 06; dryer 09 with IR radiation source or hot air; delivery 12
5. Sheet feed unit 01; primer application unit 02; non-impact printing unit 06; intermediate dryer 07 with IR radiation source for dispersion coating; coating unit 08; dryer 09 with IR radiation source or hot air; mechanical further processing unit 11; delivery 12
6. Sheet feed unit 01; offset printing unit 04; non-impact printing unit 06; intermediate dryer 07 with IR radiation source; mechanical further processing unit 11; delivery 12
7. Sheet feed unit 01; non-impact printing unit 06; dryer 09 with IR radiation source or hot air; delivery 12
8. Sheet feed unit 01; non-impact printing unit 06; intermediate dryer 07 with UV radiation source; dryer 09 with UV radiation source; delivery 12
9. Sheet feed unit 01; non-impact printing unit 06; intermediate dryer 07 with UV radiation source; dryer 09 with UV radiation source; mechanical further processing unit 11; delivery 12
10. Sheet feed unit 01; non-impact printing unit 06; intermediate dryer 07 with IR radiation source; offset printing unit 04; coating unit 08; dryer 09 with IR radiation source or hot air; delivery 12
11. Magazine feed unit 01; primer application unit 02; non-impact printing unit 06; intermediate dryer 07 with IR radiation source; coating unit 08; dryer 09 with IR radiation or hot air; delivery 12
12. Magazine feed unit 01; primer application unit 02; non-impact printing unit 06; intermediate dryer 07 with IR radiation source; dryer 09 with IR radiation source or hot air; mechanical further processing unit 11; delivery 12
13. Magazine feed unit 01; non-impact printing unit 06; intermediate dryer 07 with UV radiation source; coating unit 08; dryer 09 with UV radiation source; delivery 12

At least one of processing stations 01; 02; 03; 04; 07; 08; 09; 11; 12 that cooperates with the at least one non-impact printing unit 06 is selected to participate in the processing of sheets depending on whether the printing ink to be applied to the sheet by non-impact printing unit 06, in particular, is embodied as a water-based ink or printing ink or as a UV radiation-curing ink or printing ink. The machine arrangement is thus embodied for printing each of the sheets with a water-based printing ink or with a printing ink that cures by UV radiation.

Additional, non-inventive machine arrangements that will be explained in greater detail in reference to FIGS. 9 and 10 and that include a selection from the group of aforementioned processing stations 01; 02; 03; 04; 06; 07; 08; 09; 11; 12 provide production lines, for example, having essentially the following processing stations: sheet feed unit 01; first primer application unit 02; first dryer 121; first non-impact printing unit 06; second dryer 122; second primer application unit 126; third dryer 123; second non-impact printing unit 127; fourth dryer 124; delivery 12.

One advantageous machine arrangement mentioned as an example here has a plurality of processing stations for processing sheets, wherein a plurality of processing stations 01; 02; 03; 04; 06; 07; 08; 09; 11; 12 are arranged one behind the other in transport direction T of the sheets for inline processing of these sheets, wherein at least one of these processing stations 06 is embodied as a non-impact printing unit 06, wherein a first processing station 01 upstream of non-impact printing unit 06 in transport direction T of the sheets is embodied as a sheet feed unit 01 or as a magazine feed unit 01, wherein a processing station 08 located between first processing station 01 and non-impact printing unit 06 is embodied as a first coating unit 08, which applies a coating to each of the sheets, wherein a first dryer 07 is located between first coating unit 08 and non-impact printing unit 06, wherein a first transport cylinder assembly 17 is situated for transporting the sheets from first dryer 07 to non-impact printing unit 06, wherein a second dryer 07 is located downstream of non-impact printing unit 06 in transport direction T of the sheets, wherein a device for transferring the sheets coming from non-impact printing unit 06 to second coating unit 08 is provided, wherein a third dryer 09 is located downstream of second coating unit 08, and wherein a delivery 12 for the sheets is located downstream of the third dryer 09 in transport direction T of the sheets. In addition, a mechanical further processing unit 11 may be located between third dryer 09 and delivery 12. Further, a coating unit 03 that applies a cold foil, for example, is located upstream of non-impact printing unit 06 in transport direction T of the sheets. Non-impact printing unit 06 preferably has a plurality of individually controlled inkjet printers along the transport path of the sheets. In the active region of non-impact printing unit 06, the sheets are preferably guided such that they each rest flat on a transport apparatus, wherein the transport apparatus has a curved transport path for the sheets, at least in the active region of non-impact printing unit 06, the transport apparatus being embodied as a printing cylinder 22 in the active region of non-impact printing unit 06.

Upstream of non-impact printing unit 06 in transport direction T of the sheets, a transfer device is provided, for example, wherein the transfer device aligns the sheets, for example, at least in their axial register and/or circumferential register, so that they maintain register accuracy relative to the printing position of non-impact printing unit 06, wherein the transfer device has a suction drum 32, for example, which holds each sheet by means of suction air. This machine arrangement is embodied to print each of the sheets, in particular, with a water-based printing ink or with a printing ink that cures under ultraviolet radiation. This machine arrangement is embodied in particular for producing various packaging means. The device for transferring the sheets coming from non-impact printing unit 06 to second coating unit 08 is embodied as a second transport cylinder assembly 19, for example.

Figure 2:
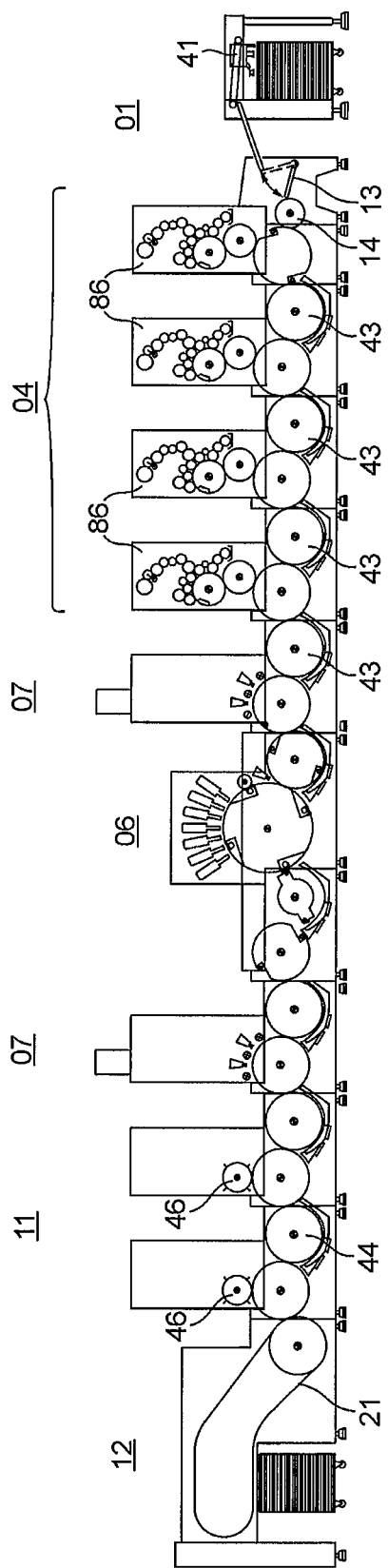
FIG. 2 shows a first machine arrangement having a plurality of different processing stations.

FIG. 2 shows as an example a machine arrangement having a plurality of processing stations 01; 02; 03; 04; 06; 07; 08; 09; 11; 12 according to production line No. 6 defined above. Sheets are gripped individually from a pile in a sheet feed unit 01 using a suction head 41, for example, and are transferred one after another in a cycle of 10,000 units per hour, for example, to an offset printing unit 04 having, for example, four printing couples 86 arranged in a row. For transferring the sheets from one printing couple 86 to the next arranged in a row, a rotating body, in particular a cylinder, preferably a transfer drum 43 is provided, each transfer drum being arranged between two immediately adjacent printing couples 86. Offset printing unit 04 receives the sheets supplied to it by sheet feed unit 01, for example, with a rocking gripper 13 and guides the sheets to a transfer drum 14 of offset printing unit 04, wherein the sheets are then guided from one printing couple 86 to the next in a gripper closure in offset printing unit 04. The sheets are printed on at least one side in offset printing unit 04. If a turning device 23 is present, the sheets can also be printed on both sides in offset printing unit 04, i.e., in perfecting printing.

After passing through processing station 04, which is embodied here as an offset printing unit 04, for example, the sheet in question, preferably printed in four colors, is transferred by means of first transport cylinder assembly 17 to a non-impact printing unit 06. Non-impact printing unit 06 preferably comprises a plurality of inkjet printers, for example five, arranged in a linear row, in particular with each being controlled individually. The sheets that have been provided with at least one static print image in offset printing unit 04 and with at least one varying or at least variable print image in non-impact printing unit 06 are then dried in a dryer 07 or intermediate dryer 07, preferably with an IR radiation source. After that, the sheets are processed further in a mechanical further processing unit 11, for example, by punching and/or creasing and/or separating copies from the respective sheet. Lastly, the sheets and/or copies separated from the sheets are collected in a delivery 12, in particular being stacked. In the active region of first gripper system 16 and/or of the first chain conveyor 16, a delivery 12, in particular a multi-pile delivery, may be provided along the transport path provided for the sheets. A multi-pile delivery is likewise arranged, for example, downstream of mechanical further processing unit 11 in transport direction T of the sheets.

The sheets picked up from a pile in feed unit 01, in particular in sheet feed unit 01, are transported individually, spaced from one another, through offset printing unit 04 at a first transport speed. Sheets transferred from offset printing unit 04 to non-impact printing unit 06 are transported in said non-impact printing unit 06 at a second transport speed, wherein the second transport speed prevailing in non-impact printing unit 06 is typically lower than the first transport speed prevailing in offset printing unit 04. To adapt the first transport speed prevailing in offset printing unit 04 to the typically lower second transport speed prevailing in non-impact printing unit 06, for example, the sheet gap existing between immediately successive sheets, i.e., the distance resulting for the sheets transported in the gripper closure through offset printing unit 04 due to the gripper channel width, for example, is preferably reduced in the transfer of these sheets from offset printing unit 04 to non-impact printing unit 06, wherein such a reduction in distance ranges from 1% to 98%, based on the original distance, for example. Thus, directly successive sheets are also transported spaced a distance from one another in non-impact printing unit 06, but with a typically smaller sheet gap or at a shorter distance than in offset printing unit 04, and consequently, also at a lower second transport speed. This second transport speed is preferably maintained when sheets that have been printed in non-impact printing unit 06 are first transported to an intermediate dryer 07 or dryer 09, and from there, e.g. by means of a feed table, to a mechanical further processing unit 11 and on to delivery 12. However, the sheets may also be changed from their second transport speed to a third transport speed, for example, if required by mechanical further processing unit 11, wherein the third transport speed is typically higher than the second transport speed and corresponds, for example, to the first transport speed prevailing in offset printing unit 04, in particular. Upstream of mechanical further processing unit 11, for example, second transport cylinder assembly 19 is provided, which grips the sheets coming from intermediate dryer 07 or dryer 09 and transports them to mechanical further processing unit 11. In the area of mechanical further processing unit 11, which comprises a plurality of processing mechanisms 46 in a row, for example, a rotating body, in particular a cylinder, preferably a transfer drum 44, is provided for transferring the sheets from one processing mechanism 46 to the next in a row, each of these rotating bodies being arranged between two neighboring processing mechanisms 46. One of the processing mechanisms 46 is embodied, for example, as a punching mechanism, and another processing mechanism 46 is embodied, for example, as a creasing mechanism. The processing mechanisms 46 in question are embodied for carrying out the mechanical further processing of the sheets, preferably in cooperation with a cylinder transporting the respective sheet. After the sheets and/or the copies separated therefrom have undergone mechanical further processing, they are transported by means of a chain conveyor 21, for example, to delivery 12, where they are collected, preferably being stacked.

The sheets are transported from the outlet of offset printing unit 04 at least up to the outlet of intermediate dryer 07 or dryer 09, preferably to the intake of mechanical further processing unit 11, by means of a multipart transport apparatus, i.e. a transport apparatus consisting of a plurality of modules, in particular transport units, arranged one behind the other in transport direction T of the sheets, wherein the transport apparatus has a plurality of transport cylinders. An intermediate dryer 07 or a dryer 09 may also be disposed between offset printing unit 04 and non-impact printing unit 06 as needed.

FIGS. 3 through 8 schematically illustrate examples of additional machine arrangements, each comprising a plurality of processing stations 01; 02; 03; 04; 06; 07; 08; 09; 11; 12, wherein the reference numerals denote processing stations 01; 02; 03; 04; 06; 07; 08; 09; 11; 12 explained above as well as additional ones of their respective assemblies.

Figure 3:
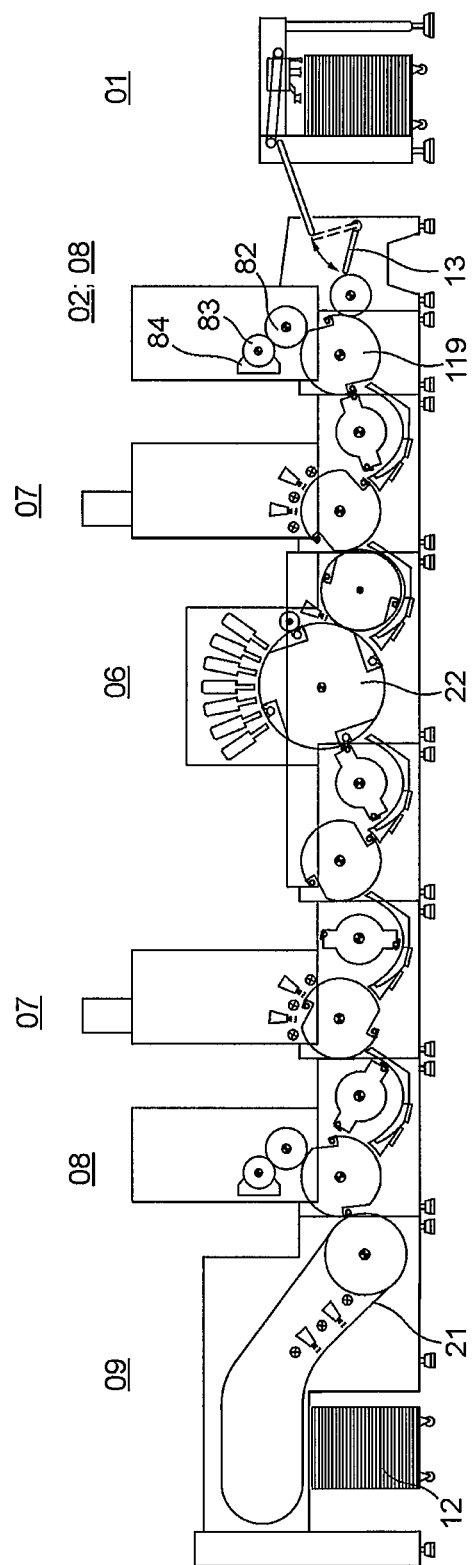
FIGS. 3 to 8 show additional machine arrangements, each having a plurality of different processing stations.

FIG. 3 shows a machine arrangement comprising the following processing stations 01; 02; 03; 04; 06; 07; 08; 09;

11; 12 arranged one behind the other in transport direction T of the printing stock: sheet feed unit 01; primer application unit 02 or coating unit 08; intermediate dryer 07; non-impact printing unit 06; intermediate dryer 07; coating unit 08; dryer 09; delivery 12.

Figure 4:
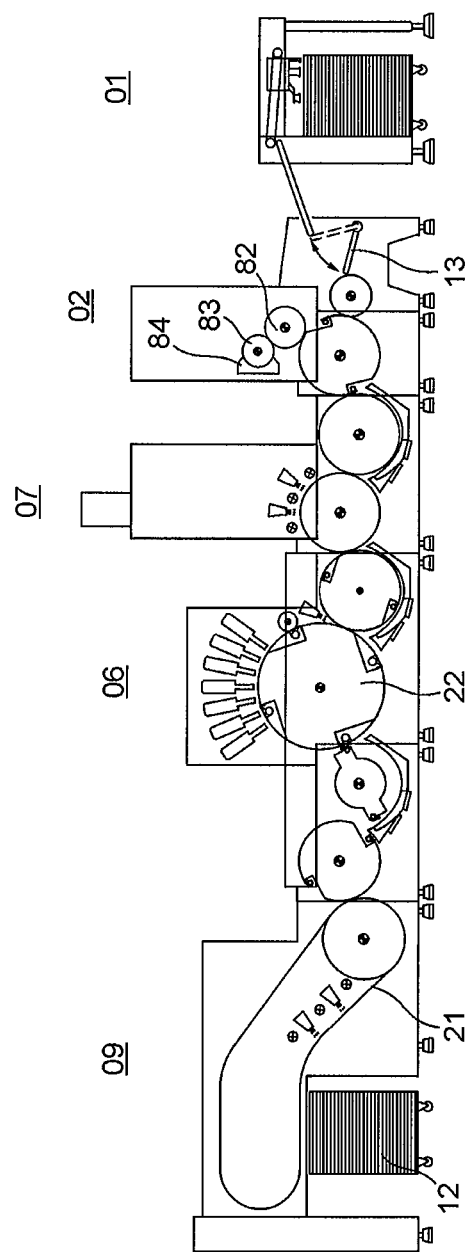

FIG. 4 shows a machine arrangement comprising the following processing stations 01; 02; 03; 04; 06; 07; 08; 09; 11; 12 arranged one behind the other in transport direction T of the printing stock: sheet feed unit 01; primer application unit 02; intermediate dryer 07; non-impact printing unit 06; dryer 09; delivery 12.

Figure 5:
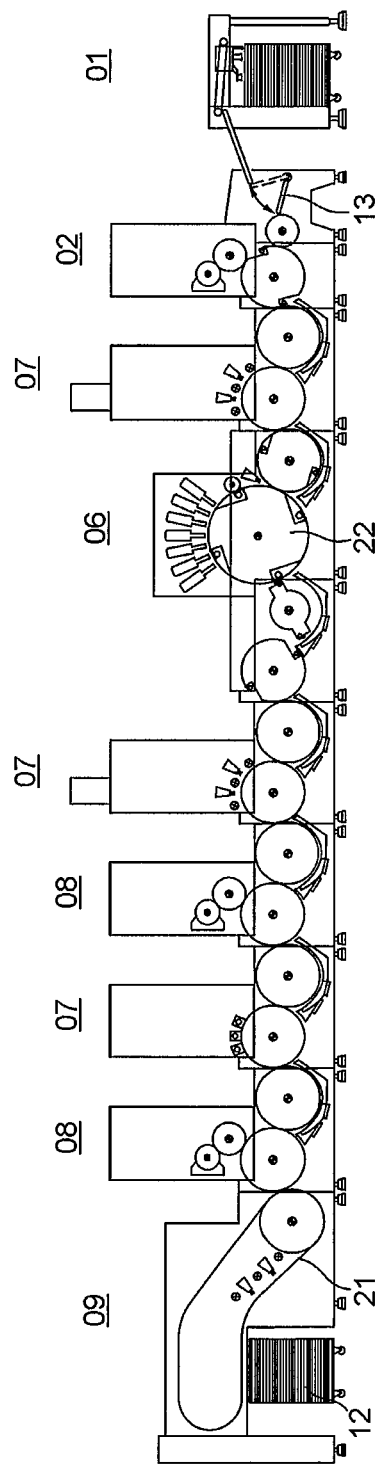

FIG. 5 shows a machine arrangement comprising the following processing stations 01; 02; 03; 04; 06; 07; 08; 09; 11; 12 arranged one behind the other in transport direction T of the printing stock: sheet feed unit 01; primer application unit 02; intermediate dryer 07; non-impact printing unit 06; intermediate dryer 07; coating unit 08; intermediate dryer 07; coating unit 08; dryer 09; delivery 12.

Figure 6:
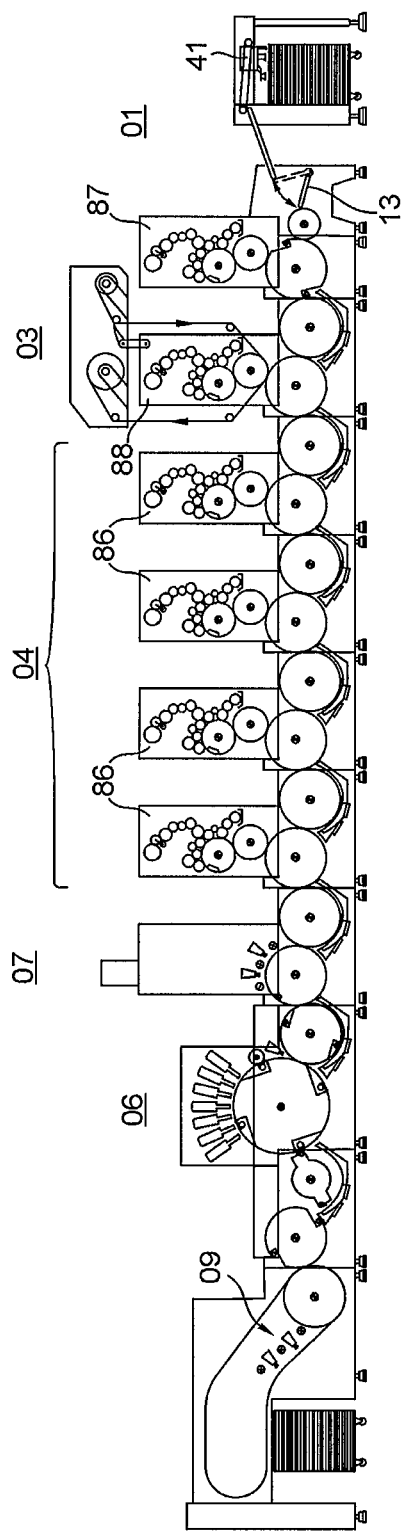

FIG. 6 shows a machine arrangement comprising the following processing stations 01; 02; 03; 04; 06; 07; 08; 09; 11; 12 arranged one behind the other in transport direction T of the printing stock: sheet feed unit 01; a first offset printing unit 04; cold foil application unit 03; four additional offset printing units 04 based on the unit construction principle; intermediate dryer 07; non-impact printing unit 06; intermediate dryer 07; non-impact printing unit 06; dryer 09; delivery 12.

Figure 7:
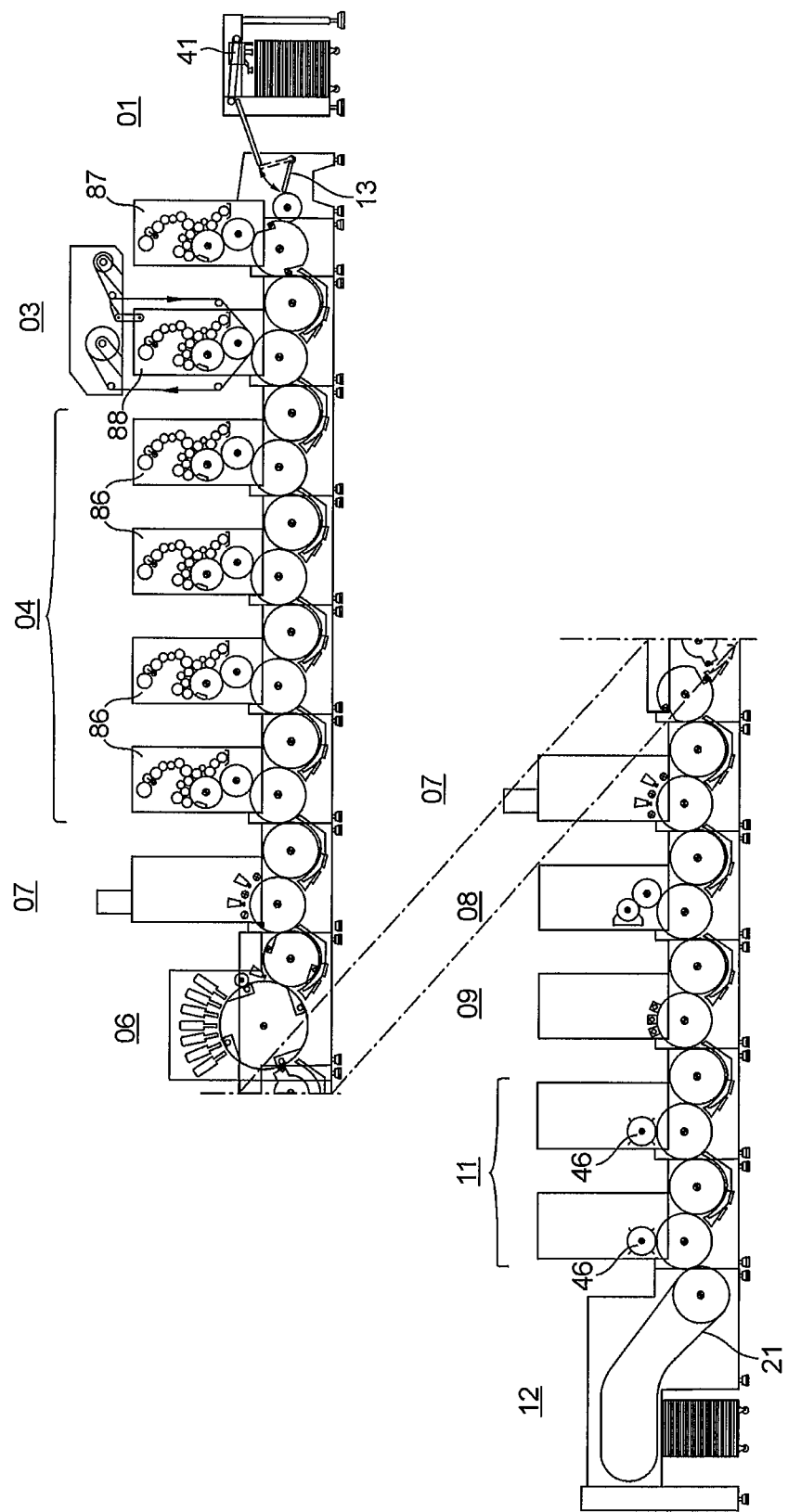

FIG. 7 shows a machine arrangement, which is shown with an offset due to its length, comprising the following processing stations 01; 02; 03; 04; 06; 07; 08; 09; 11; 12 arranged one behind the other in transport direction T of the printing stock: sheet feed unit 01; a first offset printing unit 04; cold foil application unit 03; four additional offset printing units 04 based on the unit construction principle; intermediate dryer 07; non-impact printing unit 06; intermediate dryer 07; coating unit 08; dryer 09; two mechanical further processing units 11 in the unit construction principle; delivery 12.

Figure 8:
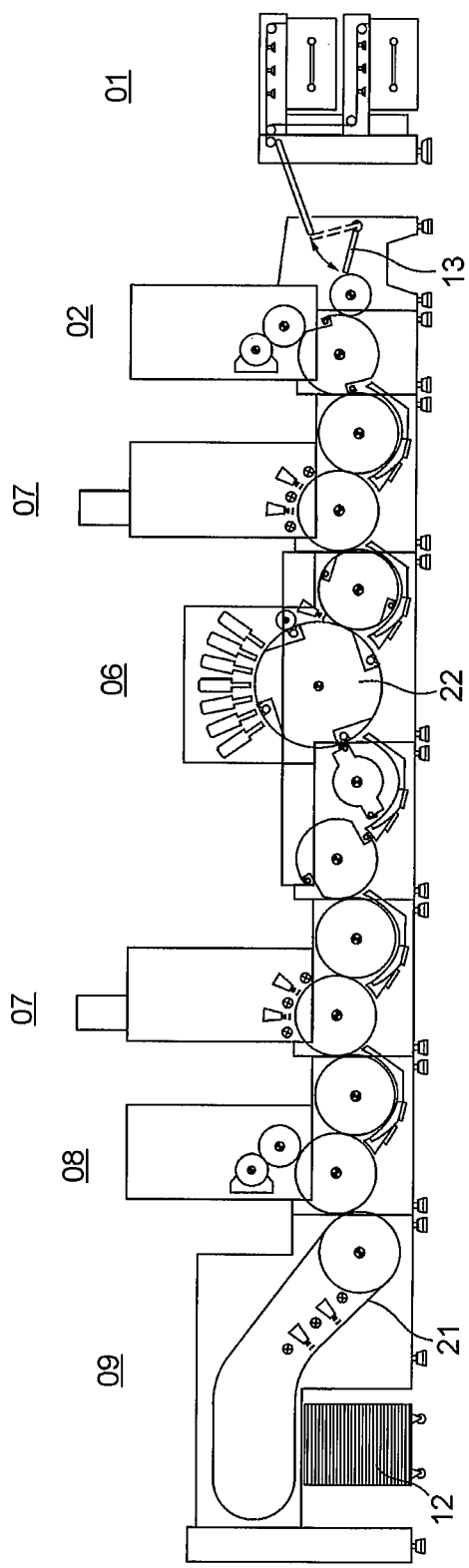

FIG. 8 shows a machine arrangement comprising the following processing stations 01; 02; 03; 04; 06; 07; 08; 09; 11; 12 arranged one behind the other in transport direction T of the printing stock: magazine feed unit 01; primer application unit 02; intermediate dryer 07; non-impact printing unit 06; intermediate dryer 07; coating unit 08; dryer 09; delivery 12.

As has already been mentioned, it is provided that with the machine arrangements described above, each comprising a plurality of processing stations 01; 02; 03; 04; 06; 07; 08; 09; 11; 12 for processing sheets and for transporting these sheets, each has at least one transport apparatus for processing sheets of different formats, i.e., of different lengths and/or widths. Thus, the sheets, which are usually rectangular, differ, e.g. in terms of their respective length, this length extending in transport direction T of the sheets in each case. When a processing station 02; 03; 04; 06; 07; 08; 09; 11; 12 embodied in particular as a non-impact printing unit 06 to which sheets are fed sequentially is used, to avoid a decrease in productivity of a machine arrangement when processing comparatively shorter sheets, i.e. sheets of a smaller format than larger-format sheets that are otherwise processed in said machine arrangement, a method having the following method steps is proposed:

A method for operating a transport apparatus for supplying a plurality of sheets sequentially to a processing station 02; 03; 04; 06; 07; 08; 09; 11; 12, wherein sheets of different lengths, said length extending in transport direction T of the sheets, are used for processing by the same processing station 02; 03; 04; 06; 07; 08; 09; 11; 12, wherein the sheets to be supplied one after another to processing station 02; 03; 04; 06; 07; 08; 09; 11; 12 are transported by the transport apparatus spaced a distance from one another, wherein the transport apparatus impresses a transport speed on each of the sheets to be transported, wherein the distance between immediately successive sheets for sheets of different lengths extending in transport direction T of these sheets is kept constant by adjusting the transport speed to be impressed upon the sheet in question by the transport apparatus, wherein the transport speed of a subsequent sheet in transport direction T is adjusted in relation to the transport speed of the sheet immediately preceding it. To achieve and/or maintain a high productivity to be rendered by processing station 02; 03; 04; 06; 07; 08; 09; 11; 12, the sheets to be supplied one after another to the relevant processing station 02; 03; 04; 06; 07; 08; 09; 11; 12 are each preferably transported by the transport apparatus at a minimal distance, but at a distance that is typically not equal to zero. The distance between successive sheets in transport direction T, i.e., between the rear edge of a preceding sheet extending transversely to transport direction T and the front edge of the immediately subsequent sheet extending transversely to transport direction T, ranges from 0.5 mm to 50 mm, for example, and is preferably less than 10 mm. If a sheet having a shorter length is to be processed after a sheet of greater length in the processing station 02; 03; 04; 06; 07; 08; 09; 11; 12 in question, the transport apparatus will accelerate the sheet having a shorter length by increasing its transport speed. Conversely, a sheet of greater length will be decelerated by the transport apparatus by decreasing its transport speed if the sheet of greater length is to be processed in the processing station 02; 03; 04; 06; 07; 08; 09; 11; 12 in question after a sheet of shorter length. A non-impact printing unit 06, the productivity of which is usually greatest when the sheets to be printed by it are supplied to it in succession at a constant minimal distance, regardless of their respective format, is preferably used as processing station 02; 03; 04; 06; 07; 08; 09; 11; 12. If a processing station 04 embodied as an offset printing unit 04, for example, is provided upstream of non-impact printing unit 06 in a machine arrangement, then regardless of their format, sheets printed in offset printing unit 04 will be supplied to the transport apparatus at a transport speed corresponding to a production speed of this offset printing unit 04, with this transport speed, which is predetermined for these sheets by offset printing unit 04, being adapted as they are transported by the transport apparatus to the transport speed that corresponds to the processing speed of non-impact printing unit 06. If these sheets will additionally be supplied to non-impact printing unit 06 at a constant distance from one another regardless of their format, then sheets of greater length are decelerated less than shorter sheets, but in any case, a reduction in their respective transport speed will be necessary because the processing speed of non-impact printing unit 06 is typically lower than the production speed of offset printing unit 04.

Each sheet is preferably held in a force-locking manner, for example by suction air and/or by grippers, during its transport by the transport apparatus. In the preferred embodiment, the transport speed to be impressed on the sheet in question is adjusted by a preferably electronic control unit, wherein the control unit performs the adjustment of the transport speed in particular to maintain a constant distance between successive sheets, for example, in a control loop. It is provided, for example, that a sheet to be supplied to mechanical further processing unit 11 is brought by rocking gripper 13 and transfer drum 31 from the second transport speed to the third transport speed, meaning that the sheet in question is accelerated in particular by the rotation of transfer drum 31 controlled by the control unit.

Figure 9:
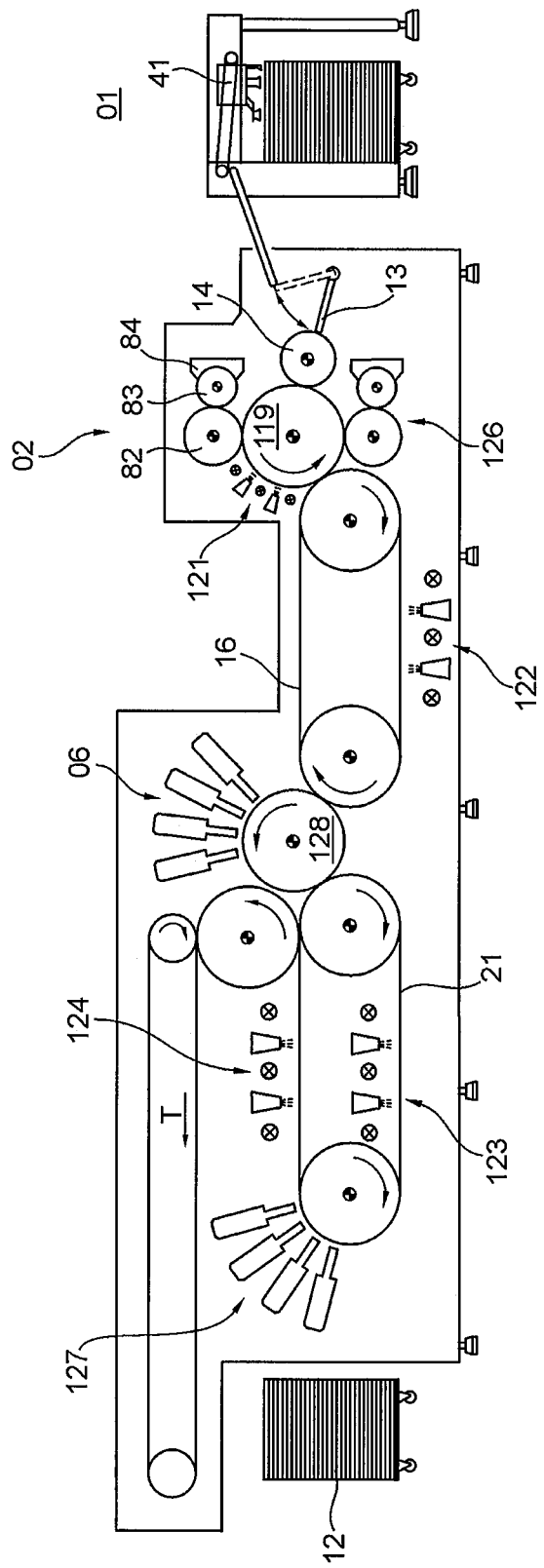
FIG. 9 shows a machine arrangement for two-sided sequential processing of a plurality of sheet-type substrates.

FIG. 9 shows another non-inventive machine arrangement comprising a plurality of processing stations, typically different ones, for the sequential processing of a plurality of sheet-type substrates. The flat substrates, each having a front side and a back side, are gripped by a suction head 41, for example, in a feed unit 01 and are transferred individually by means of a rocking gripper 13 to a transfer drum 14 and from there to a rotating impression cylinder 119, wherein this impression cylinder 119 receives on its circumferential surface at least one of these substrates or a plurality thereof, for example, two or three substrates, arranged in succession in the circumferential direction. Each of the substrates to be transported is held on the circumferential surface of impression cylinder 119 by means of at least one retaining element embodied as a gripper, for example. In particular, flexible and/or thin substrates with a thickness of up to 0.1 mm, for example, or max. 0.2 mm can also be held by suction air on the circumferential surface of impression cylinder 119, for example, wherein the positioning of such a substrate against the circumferential surface of impression cylinder 119, in particular along the edges of the substrate, is supported, for example, by blower air directed in particular radially toward the circumferential surface of impression cylinder 119. Proceeding from the transfer drum 14, which is set against this impression cylinder 119, first a first primer application unit 02 for priming the front side and, following this first primer application unit 02, a second primer application unit 126 for priming the back side of the same sheet-type substrate is thrown onto impression cylinder 119 in its direction of rotation, which is indicated by a rotational direction arrow in FIG. 9, wherein the second primer application unit 126 primes the back side of the substrate in question indirectly, for example, in particular by a reverse transfer of the primer applied by this second primer application unit 126 to the circumferential surface of impression cylinder 119 and from this circumferential surface onto the back side of the substrate in question. The front side and/or back side of the substrate in question may be primed over its full surface or in partial areas as needed. Impression cylinder 119 transfers a substrate that has been primed on both sides to a first transport apparatus, for example, a transport apparatus having at least one drawing element, in particular a continuously revolving transport apparatus, to a first chain conveyor 16, for example, wherein this first transport apparatus transports this substrate to a first non-impact printing unit 06, wherein this first non-impact printing unit 06 at least partially prints the front side of the substrate in question. The first non-impact printing unit 06 transfers the substrate, which has been printed on the front side, to a second transport apparatus, for example, a transport apparatus having at least one drawing element, in particular revolving continuously, for example, to a second chain conveyor 21, wherein this second transport apparatus receives the substrate in question, in the area of its first chain wheel, for example. In the area of the second chain wheel of this second chain conveyor 21, for example, a second non-impact printing unit 127 is disposed, wherein this second non-impact printing unit 127 at least partially prints the back side of the substrate in question, which has previously been printed on the front side. Thus, first non-impact printing unit 06 and second non-impact printing unit 127 are arranged one behind the other at different positions along the transport path of the substrate in question in transport direction T of the respective sheet-type substrate. The substrate in question, now printed on both sides, is then dropped onto a pile in a delivery 12.

The machine arrangement for processing the substrate in question on both sides, illustrated in FIG. 9, has a plurality of dryers 121; 122; 123; 124, preferably four, namely a first dryer 121 for drying the primer applied to the front side of the substrate in question, and a second dryer 122 for drying the primer applied to the back side of the substrate in question. In addition, a third dryer 123 is provided for drying the substrate in question that has been printed on the front side by first non-impact printing unit 06, and a fourth dryer 124 is provided for drying the substrate in question that has been printed on the back by second non-impact printing unit 127. Dryers 121; 122; 123; 124, which are identical, for example, are embodied for drying the substrate in question, for example, by irradiation with infrared or ultraviolet radiation, with the type of radiation being dependent, in particular, upon whether the ink or printing ink applied to the substrate in question is water-based or UV curing. Transport direction T of the substrate in question transported through the machine arrangement is indicated by arrows in FIG. 9. The first non-impact printing unit 06 and the second non-impact printing unit 127 are each embodied, for example, as at least one inkjet printing unit. In the active region of first non-impact printing unit 06, a third transport apparatus is provided, which receives the substrate in question, primed on both sides, from the first transport apparatus, transports it to the second transport apparatus and delivers it to this second transport apparatus. The third transport apparatus that transports the substrate in question within the active region of first non-impact printing unit 06 is embodied as a transport cylinder 128, wherein the preferably multiple inkjet printing units of the first non-impact printing unit 06 are each arranged radially to this transport cylinder 128.

The third transport apparatus for transporting the substrate in question within the active region of the first non-impact printing unit 06 and the second transport apparatus for transporting the substrate in question within the active region of the second non-impact printing unit 127 preferably each have one dedicated drive, each of these dedicated drives being embodied as a motor that is preferably electrically driven and is adjusted or at least adjustable in terms of its rotational speed and/or angular position, wherein the printing of the substrate in question on its front side by first non-impact printing unit 06 and on its back side by second non-impact printing unit 127 is or at least can be synchronized by means of these dedicated drives that influence the respective transport apparatuses in terms of their motion behavior.

In a preferred embodiment, first dryer 121 for drying the primer that has been applied to the front side of the substrate in question is located in the region of impression cylinder 119, for example. Second dryer 122 for drying the primer that has been applied to the back side of the substrate in question is preferably located in the region of the first transport apparatus. Third dryer 123 for drying the substrate in question that has been printed on the front side by first non-impact printing unit 06 is located in the region of the second transport apparatus or is situated in the region of the third transport apparatus, which is in turn situated in the active region of first non-impact printing unit 06 and cooperates with it. Fourth dryer 124 for drying the substrate in question that has been printed on the back by second non-impact printing unit 127 is located downstream of the third transport apparatus in transport direction T of the substrate in question that is transported through the machine arrangement, for example.

The machine arrangement illustrated in FIG. 9 can also be described as a machine arrangement for the sequential processing of a plurality of sheet-type substrates each having a front side and a back side, wherein a first non-impact printing unit 06 and a second non-impact printing unit 127 as well as a first primer application unit 02 and a second primer application unit 126 are provided, wherein in each case with respect to the same sheet-type substrate, first primer application unit 02 is situated for priming the front side and second primer application unit 126 is situated for priming the back side, and wherein with respect to this substrate, first non-impact printing unit 06 is situated for printing the front side that has been primed by first primer application unit 02, and second non-impact printing unit 127 is situated for printing the back side that has been primed by the second primer application unit 126. A first dryer 121 for drying the primer that has been applied to the front side of the substrate in question is provided upstream of first non-impact printing unit 06 in transport direction T of the substrate in question, and a second dryer 122 for drying the primer that has been applied to the back side of the substrate in question is arranged upstream of second non-impact printing unit 127 in transport direction T of the substrate in question, and a third dryer 123 for drying the substrate in question that has been printed on the front side by first non-impact printing unit 06 is provided downstream of first non-impact printing unit 06 in transport direction T of the substrate in question, and a fourth dryer 124 for drying the substrate in question that has been printed on the back side by second non-impact printing unit 127 is provided downstream of second non-impact printing unit 127 in transport direction T of the substrate in question.

The second primer application unit 126 may optionally be located upstream or downstream of second non-impact printing unit 127 in transport direction T of the substrate in question. First dryer 121 for drying the primer applied to the front side of the substrate in question, and/or second dryer 122 for drying the primer applied to the back side of the substrate in question, and/or third dryer 123 for drying the substrate in question that has been printed by first non-impact printing unit 06 and/or fourth dryer 124 for drying the substrate in question that has been printed on the back side by second non-impact printing unit 127 are each embodied, for example, as a dryer that dries the primed and/or printed substrate in question using hot air and/or by irradiation with infrared or ultraviolet radiation, wherein dryer 121; 122; 123; 124 that dries the primed and/or printed substrate in question by irradiation with infrared or ultraviolet radiation is preferably embodied as an LED dryer, i.e., as a dryer that uses semiconductor diodes. In addition, at least one transport apparatus for transporting the substrate in question is provided, wherein this transport apparatus is embodied as a transport cylinder or as a revolving transport belt or as a chain conveyor. The at least one transport apparatus for transporting the substrate in question has at least one retaining element, wherein the at least one retaining element is embodied to hold the substrate in question in a force-locking or a form-fitting manner.

Figure 10:
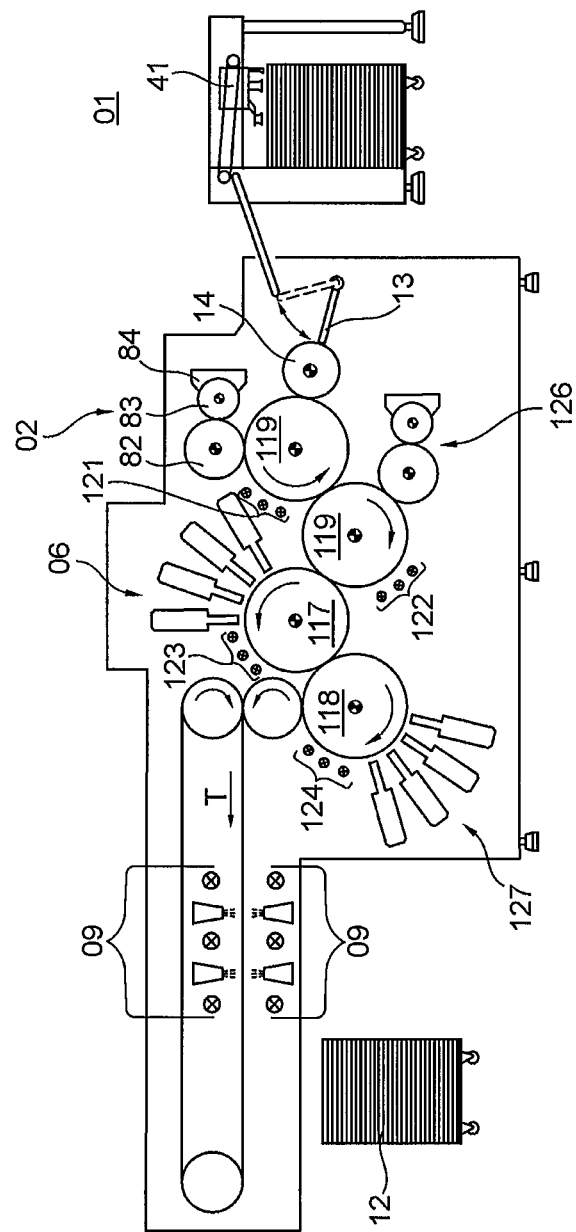
FIG. 10 shows another machine arrangement without a turning device for two-sided sequential processing of a plurality of sheet-type substrates.

FIG. 10 shows yet another advantageous, non-inventive, machine arrangement for the sequential processing of a plurality of sheet-type substrates each having a front side and a back side. This machine arrangement, preferably embodied as a printing machine, in particular as a sheet-fed printing machine, comprises at least one first printing cylinder 117 and one second printing cylinder 118. At least one first non-impact printing unit 06 for printing on the front side of the substrate in question, and, downstream of the first non-impact printing unit 06 in the direction of rotation of the first printing cylinder 117, a dryer 123 that dries the front side of the substrate in question that has been printed by first non-impact printing unit 06 are provided, each on the periphery of the first printing cylinder 117, and at least one second non-impact printing unit 127 for printing on the back side of the substrate in question, and, downstream of the second non-impact printing unit 127 in the direction of rotation of the second printing cylinder 118, a dryer 124 for drying the back side of the substrate in question that has been printed by the second non-impact printing unit 127 are provided, each on the periphery of the second printing cylinder 118. First non-impact printing unit 06 and second non-impact printing unit 127 are each embodied, e.g. as at least one inkjet printing unit. First non-impact printing unit 06 and/or second non-impact printing unit 127 each print in a plurality of printing inks, for example, four printing inks, in particular the printing inks yellow, magenta, cyan and black, wherein a specific inkjet printing unit is preferably provided for each of these printing inks in each of the non-impact printing units 06; 127 in question.

In the machine arrangement according to FIG. 10, first printing cylinder 117 and second printing cylinder 118 are arranged such that they form a common roller nip, wherein in this common roller nip, first printing cylinder 117 transfers the substrate in question, which has been printed on the front side and dried, directly to second printing cylinder 118. In the preferred embodiment of this machine arrangement, a first primer application unit 02 and a second primer application unit 126 are also provided, wherein the first primer application unit 02 is arranged to prime the front side and the second primer application unit 126 is arranged to prime the back side of the same sheet-type substrate in each case, wherein with respect to this substrate, first non-impact printing unit 06 is arranged to print the front side that has been primed by first primer application unit 02, and second non-impact printing unit 127 is arranged to print the back side that has been primed by second primer application unit 126. First primer application unit 02 and second primer application unit 126 each comprise an impression cylinder 119, for example, wherein these two impression cylinders 119 are arranged to form a common roller nip, wherein in this common roller nip, the impression cylinder 119 that has the first primer application unit 02 transfers the substrate in question directly to the impression cylinder 119 that has the second primer application unit 126. The impression cylinder 119 that has the second primer application unit 126 and the first printing cylinder 117 that has the first non-impact printing unit 06 are arranged to form a common roller nip, wherein the impression cylinder 119 that has the second primer application unit 126 transfers the substrate in question directly to the first printing cylinder 117 that has the first non-impact printing unit 06.

A dryer 121 for drying the front side of the substrate in question that has been primed by the first primer application unit 02 is disposed on the periphery of the impression cylinder 119 that has this first primer application unit 02, typically directly downstream of the first primer application unit 02, for example, and/or a dryer 122 for drying the back side of the substrate in question that has been primed by the second primer application unit 126 is arranged on the periphery of the impression cylinder 119 that has this second primer application unit 126, typically immediately downstream of the second primer application unit 126. Dryer 121 for drying the primer applied to the front side of the substrate in question, and/or dryer 122 for drying the primer applied to the back side of the substrate in question, and/or dryer 123 for drying the substrate in question that has been printed on the front side by first non-impact printing unit 06, and/or dryer 124 for drying the substrate in question that has been printed on the back side by second non-impact printing unit 127 is/are each embodied as a dryer that dries the primed and/or printed substrate in question using hot air and/or by irradiation with infrared or ultraviolet radiation. In a particularly preferred embodiment, dryer 121; 122; 123; 124 that dries the primed and/or printed substrate in question by irradiation with infrared or ultraviolet radiation is embodied as an LED dryer, i.e., as a dryer that generates infrared or ultraviolet radiation by means of semiconductor diodes.

Moreover, in the machine arrangement according to FIG. 10, first printing cylinder 117 and second printing cylinder 118 and the impression cylinder 119 that has first primer application unit 02 and the impression cylinder 119 that has second primer application unit 126 are each connected to one another, preferably in a single drive train formed from gear wheels, i.e., in a gear train, and are driven jointly in their respective rotation by a single drive, wherein this drive is preferably embodied as an electric motor, in particular as a speed-controlled and/or position-controlled electric motor. First printing cylinder 117 and second printing cylinder 118 and the impression cylinder 119 that has first primer application unit 02 and the impression cylinder 119 that has second primer application unit 126 are each embodied as multiple-sized, for example, i.e., a plurality of substrates, e.g. two or three or four, is or at least can be arranged one behind the other in the circumferential direction on their circumferential surface. Each one of the substrates to be transported is retained in a force-locking and/or form-fitting manner on the circumferential surface of first printing cylinder 117 and/or of second printing cylinder 118 and/or of the impression cylinder 119 that has first primer application unit 02 and/or of the impression cylinder 119 that has second primer application unit 126, the retention being by means of at least one retaining element embodied as grippers, for example. In particular, flexible and/or thin substrates having a thickness of up to 0.1 mm, for example, or max. 0.2 mm may be held in a force-locking manner, for example, by means of suction air on the circumferential surface of the cylinder 117; 118; 119 in question, wherein the positioning of such a substrate against the circumferential surface of the cylinder 117; 118; 119 in question, in particular along the edges of this substrate, is supported, for example, by blower air directed in particular radially toward the circumferential surface of the cylinder 117; 118; 119 in question.

The substrate in question that has been printed on both sides is then preferably transported, following its transport through second printing cylinder 118, by means of a transport apparatus to a delivery 12, for example, and is deposited onto a pile in delivery 12. The transport apparatus connected to second printing cylinder 118 is embodied, for example, as a chain conveyor, wherein the substrate in question is preferably dried again on both sides by means of at least one dryer 09 during its transport by this transport apparatus and before being deposited in delivery 12. In some production lines, the intention may be for the substrate in question that has already been printed on the front side by first non-impact printing unit 06 and/or on the back side by second non-impact printing unit 127 to be printed on one or both sides with additional printing inks, in particular special inks, and/or surface finished by a coating application, for example. In this latter case, following second printing cylinder 118, upstream of the transport apparatus for transporting the substrate in question to delivery 12, at least one additional printing cylinder is provided, for example a third printing cylinder, or preferably at least one additional cylinder pair formed by a third printing cylinder and a fourth printing cylinder, on which at least one additional printing cylinder, for example a third and/or a fourth printing cylinder, is arranged in the same manner as on first printing cylinder 117 and/or on second printing cylinder 118, each in turn forming an additional printing unit, in particular an additional non-impact printing unit, or at least one coating unit 08, each optionally having an additional dryer. All of these printing cylinders aligned in a row then form a continuous transport path for the substrate in question in the machine arrangement in question, in which this substrate is then transferred from one printing cylinder to the next. The substrate in question can be processed, in particular printed, on both sides, without requiring a turning unit 23 for this substrate in this machine arrangement. The proposed machine arrangement is thus very compact and inexpensively constructed. The machine arrangement illustrated in FIG. 10 is particularly advantageous in combination with UV curing inks, for example, in printing packaging for food items or cosmetics.

Figure 11:
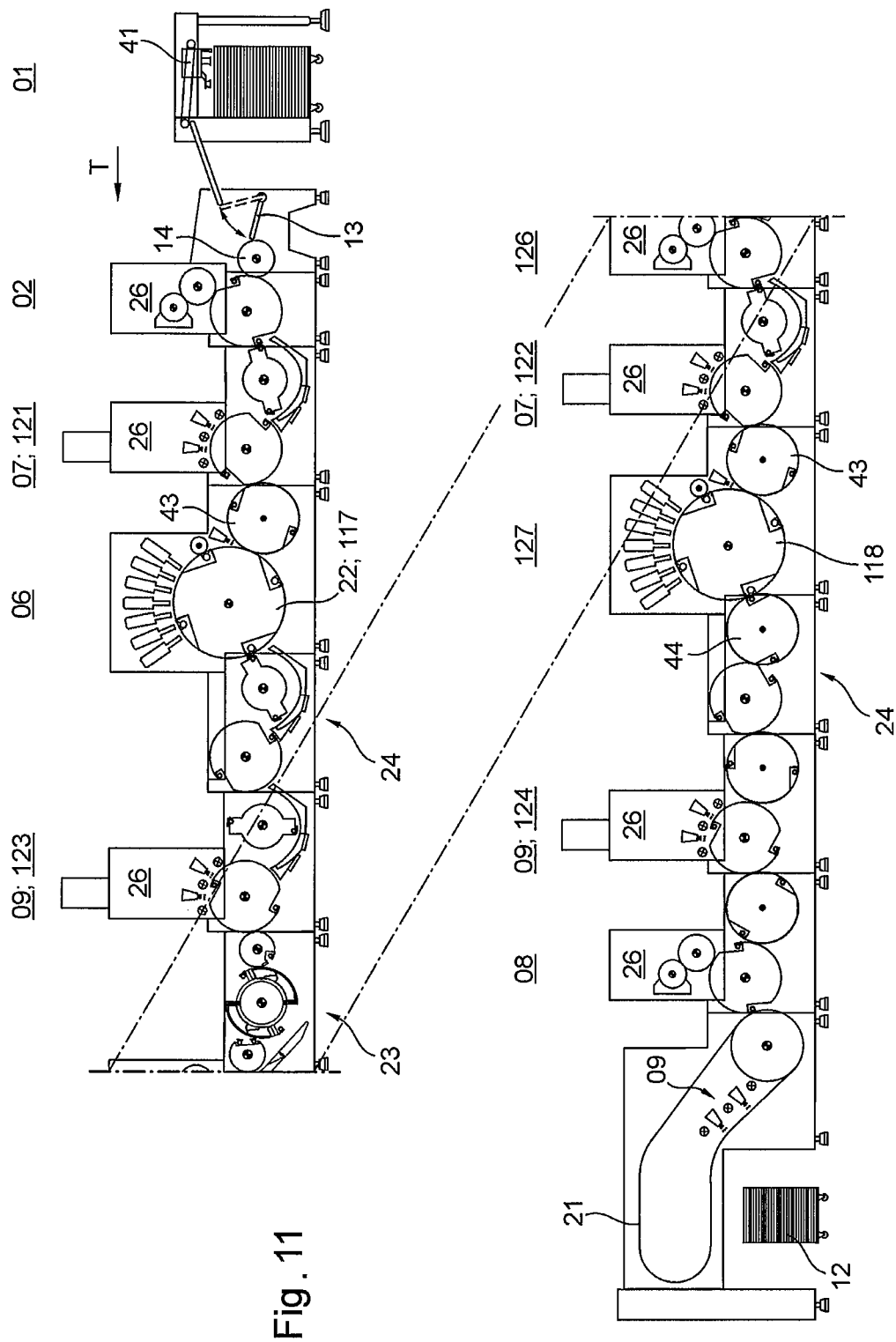
FIG. 11 shows yet another machine arrangement having a turning device for two-sided sequential processing of a plurality of sheet-type substrates.

FIG. 11 shows as an example a machine arrangement comprising a plurality of processing stations 01; 02; 03; 04; 06; 07; 08; 09; 11; 12, the processing stations 01; 02; 03; 04; 06; 07; 08; 09; 11; 12 being arranged one behind the other in transport direction T of the substrates. Each of the processing stations 01; 02; 03; 04; 06; 07; 08; 09; 11; 12 is embodied as an independently functional module, with each of the modules forming a machine unit installed in its own frame. In the preferred embodiment, the modules that are embodied as a coating unit 02; 03; 08 (i.e., primer application unit 02; 126, cold foil application unit 03 and coating unit 08) or as a dryer 07; 09; 121; 122; 123; 124 or as a printing unit 04; 06; 127 or as a mechanical further processing unit 11 each has a substrate guide unit 24 and a substrate processing unit 26. The substrate guide unit 24 has a transport cylinder assembly 17; 19 for transporting the substrates, for example, or one or more transport cylinders 128 or one or more transfer drums 43; 44. Substrate processing unit 26 comprises the actual coating unit 02; 03; 08 or dryer 07; 09; 121; 122; 123; 124 or at least one printing forme 86; 87; 88 of printing unit 04; 06; 127 or at least one processing unit 46 of mechanical further processing unit 11, depending on the type of processing station 01; 02; 03; 04; 06; 07; 08; 09; 11; 12 in each case.

The machine arrangement illustrated in FIG. 11 is a machine arrangement for perfecting printing and, starting from a feed unit 01 embodied as a sheet feed unit 01 or a magazine feed unit 01 that grips stacked substrates one after another with a suction head 41, for example, and from a downstream rocking gripper 13 with a transfer drum 14, comprises a coating unit 02; 03; 08, in particular in the form of a first primer application unit 02, followed by a first dryer 07; 121, one behind the other in transport direction T of the substrates (sheets). The substrates pretreated on the front side in this way are then each sent to a first non-impact printing unit 06 for printing the front side of the substrates with a first printing cylinder 22; 117, wherein this first printing cylinder 22; 117 is preferably embodied as triple-sized or quadruple-sized, which means that this first printing cylinder 22; 117 has at least enough retaining elements on its periphery that three or four substrates are or at least can be arranged such they are held in a force-locking manner and/or in a form-fitting manner one behind the other on its periphery. As a rule, at least one retaining element is assigned to each substrate to be held on the periphery of printing cylinder 22; 117, wherein retaining elements that are assigned to different substrates can each be operated separately, i.e., independently of one another. Retaining elements embodied as grippers are disposed in a channel, in particular, each channel extending axially on the circumferential surface of the printing cylinder 22; 117 in question. This means that, for example, if four substrates can be arranged along the periphery of printing cylinder 22; 117, the printing cylinder 22; 117 in question will have four channels, with at least one retaining element being disposed in each channel. It is also possible for at least two retaining elements to be arranged in a channel, wherein one of these retaining elements holds an edge of a first one of these substrates, said edge being at the rear in transport direction T of the substrates, and another one of these retaining elements holds a front edge of a second substrate directly following the first substrate on the periphery of the printing cylinder 22; 117 in question, said edge being at the front in transport direction T of the substrates. Preferably, a plurality of inkjet printing units is arranged one behind the other along a part of the periphery of first printing cylinder 22; 117. In the preferred embodiment, a substrate guide unit 24 embodied as a simple transport module without an additional substrate processing unit 26 follows the first non-impact printing unit 06. This transport module is also mounted in a separate frame. In this machine arrangement, this substrate guide unit 24 allows the formation of a sufficiently wide transverse gallery which in turn improves accessibility to first non-impact printing unit 06, for example, for maintenance and/or repair work. Downstream of substrate guide unit 24, a second dryer 09; 123 for drying the printed front side of the substrates is provided. Second dryer 09; 123 is followed by a turning device 23, which makes it possible for the back side of the substrates to be printed subsequently. As described previously for front side printing, i.e., for printing the front side, the substrates coming from turning device 23 are sent first to a second primer application unit 126 which treats the back side of the substrates, and then to a third dryer 07; 122. This is followed by a second non-impact printing unit 127, which prints the back side of the substrates with a second printing cylinder 118, wherein this second printing cylinder 118 is again preferably embodied as triple-sized or quadruple-sized, which means that this second printing cylinder 118 has on its periphery enough retaining elements that three or four substrates are or at least can be arranged one behind the other and held in a force-locking and/or form-fitting manner. Along part of the periphery of second printing cylinder 118, a plurality of inkjet printing units is preferably arranged one behind the other. For the same reason as has already been explained, a substrate guide unit 24 is preferably also located downstream of second non-impact printing unit 127 without an additional substrate processing unit 26. This is followed by a fourth dryer 09; 124 for drying the printed back side of the substrates. In the preferred embodiment, this is followed by a coating unit 08. The coated substrates are then dried in an additional dryer 09, wherein this dryer 09 is arranged, for example, in the transport path of a transport apparatus embodied as a chain conveyor 21, wherein this transport apparatus transports the substrates to a delivery 12, in particular to a multi-pile delivery, and are delivered there. In the machine arrangement of FIG. 11 the substrate guide units 24, each having a transport cylinder assembly 17; 19, apart from the two printing cylinders 22; 117; 118, are preferably each embodied as double-sized, so that two substrates are or at least can be arranged one behind another on the periphery of the transport cylinder 128 or the transfer drums 43; 44.

Figure 12:
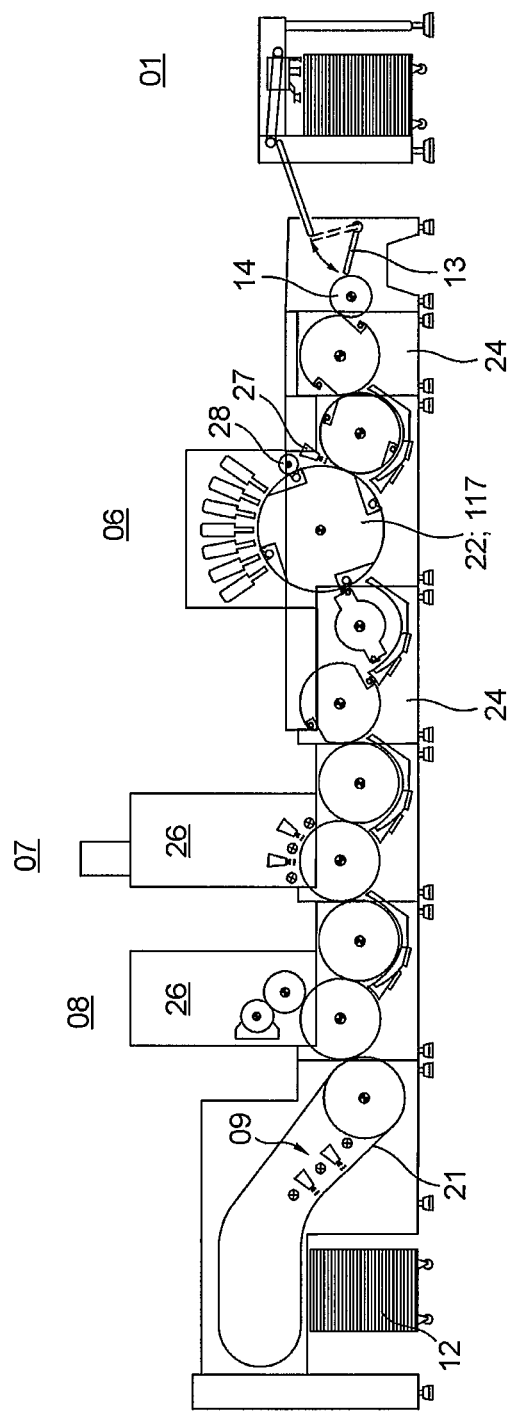
FIG. 12 shows a machine arrangement having substrate guide elements of different lengths.

FIG. 12 shows as an example a machine arrangement for one-sided processing of substrates, in particular for the one-sided printing thereof. The substrates coming from a feed unit 01 are transferred by means of a rocking gripper 13 to a transfer drum 14 and from there are fed via a substrate guide unit 24 having, for example, only a single transport cylinder 128 or only a single transfer drum 43; 44 to a non-impact printing unit 06 having a triple-sized or quadruple-sized printing cylinder 22; 117, which prints the front side of each of the substrates. To improve the positioning of the substrates against the circumferential surface of printing cylinder 22; 117, for example, a blower air device 27 and/or a pressing element 28, for example, in the form of a smoothing roller are provided. This is followed by a substrate guide unit 24 with a transport cylinder assembly 17; 19 having at least two transport cylinders 128 or transfer drums 43; 44. These are then followed by a dryer 07 and a coating unit 08. The coated substrates are then dried in an additional dryer 09, wherein this dryer 09 is again arranged, for example, in the transport path of a transport apparatus embodied as a chain conveyor 21, wherein this transport apparatus transports the substrates to a delivery 12 and delivers them there. Substrate guide units 24, apart from printing cylinders 22; 117, preferably have transport cylinders 128 or transfer drums 43; 44 that are each embodied as double-sized. A substrate guide unit 24 with a transport cylinder assembly 17; 19 having at least two transport cylinders 128 or transfer drums 43; 44 extends in transport direction T of the substrates over a length corresponding to at least one-and-a-half times the diameter of the transport cylinder 128 or transfer drum 43; 44 in question.

Figure 13:
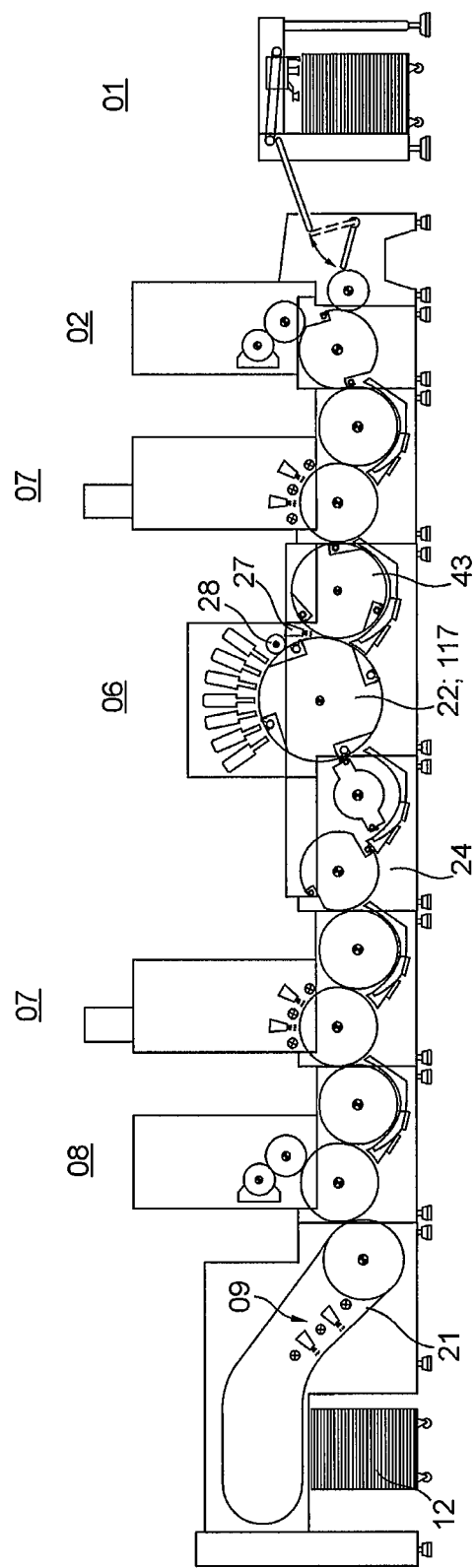
FIGS. 13 to 15 show machine arrangements having a printing cylinder and a transfer drum in various formats.
Figure 14:
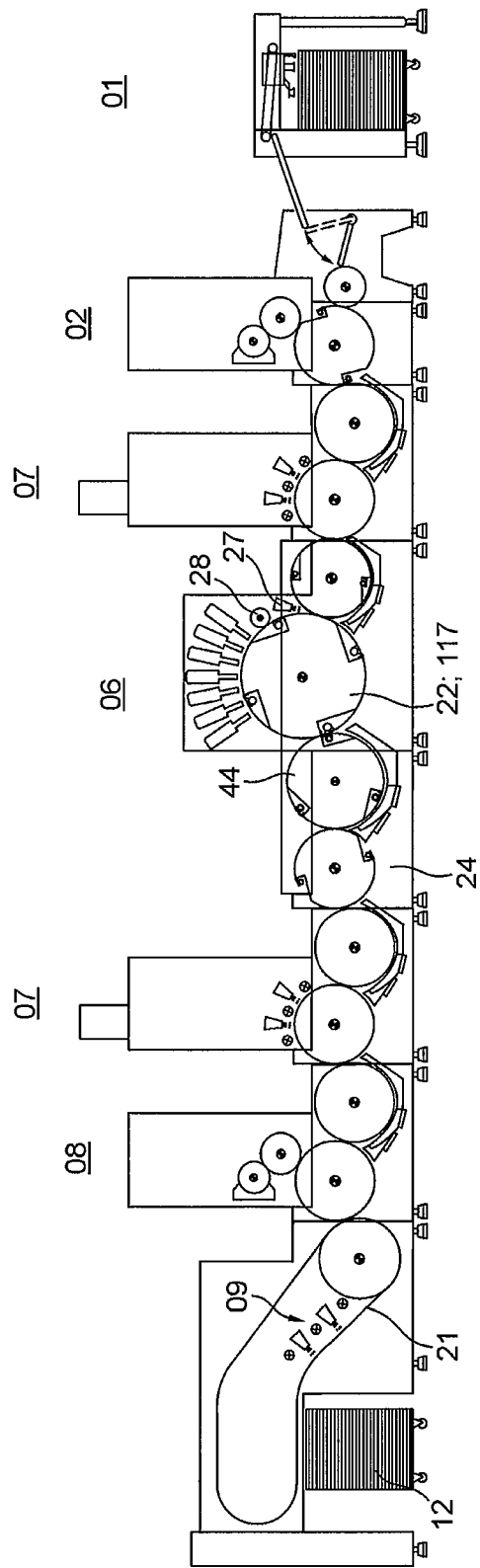
Figure 15:
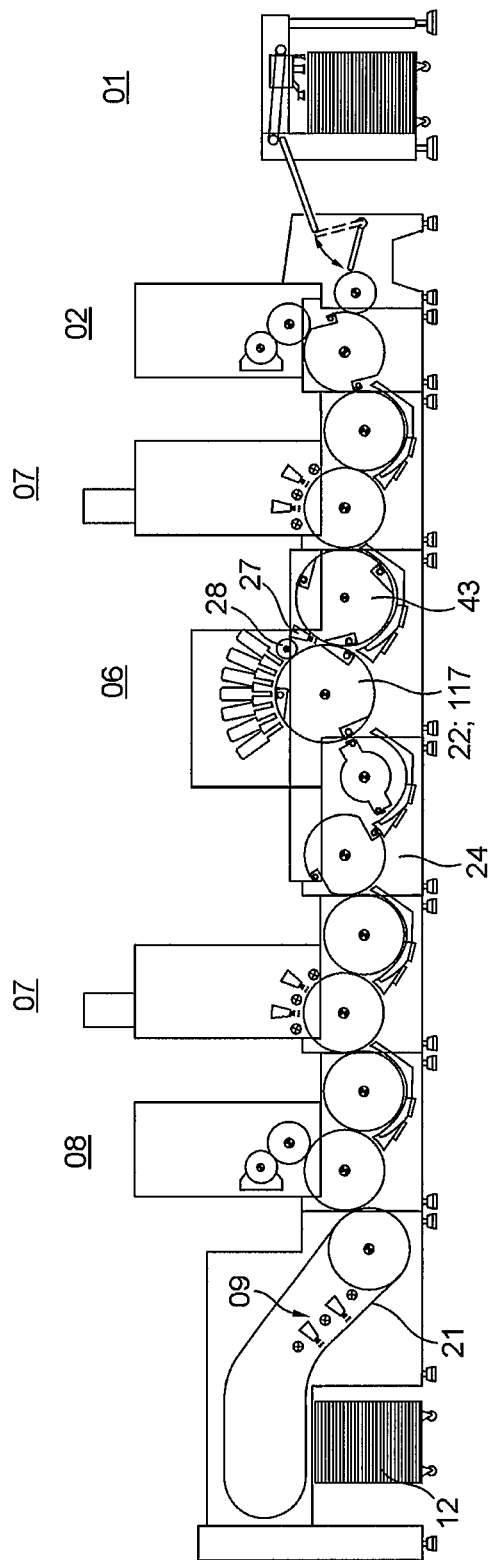

FIGS. 13 to 15 each show as an example a machine arrangement for the one-sided processing of substrates, in particular for the one-sided printing thereof, wherein a primer application unit 02 and a dryer 07 are provided downstream of feed unit 01. These are followed in the machine arrangement by a non-impact printing unit 06, a substrate guide unit 24, another dryer 07, a coating unit 08 and a dryer 09 arranged, for example, in the transport path of a transport apparatus embodied as a chain conveyor 21, wherein this transport apparatus transports the substrates to a delivery 12 and delivers them there.

In the machine arrangement of FIG. 13, printing cylinder 22; 117 is embodied as quadruple-sized. The quadruple-sized printing cylinder 22; 117 receives the substrates to be printed from a transfer drum 43 immediately upstream, which is embodied as triple-sized. In the machine arrangement of FIG. 14, printing cylinder 22; 117 is likewise embodied as quadruple-sized, however quadruple-sized printing cylinder 22; 117 transfers the printed substrates to a transfer drum 44 directly downstream of this printing cylinder 22; 117 and embodied as triple-sized. FIG. 14 shows the quadruple-sized embodiment of printing cylinder 22; 117, with a double-sized embodiment of transfer drum 43 directly upstream of this printing cylinder 22; 117. The circumferential surface of printing cylinder 22; 117 and transfer drum 43 are preferably arranged in physical contact with one another due to the formation of a common roller strip 32. In the non-inventive machine arrangement of FIG. 15, printing cylinder 22; 117 and the transfer drum 43 immediately upstream of this printing cylinder 22; 117 are each embodied as triple-sized. The machine arrangements of FIGS. 13 to 15 each differ in terms of the format of printing cylinder 22; 117 and a transfer drum 43; 44 immediately upstream or downstream of this printing cylinder 22; 117. A printing cylinder 22; 117 embodied as quadruple-sized has a diameter of approx. 1200 mm, for example. A transfer drum 43 embodied as double-sized has a diameter of approx. 600 mm, for example. The format of printing cylinder 22; 117 and the format of a transfer drum 43; 44 immediately upstream or downstream of this printing cylinder 22; 117 are determined by the number of retaining elements arranged on the respective circumference of each, wherein the retaining elements hold each of the substrates in a force-locking and/or a form-fitting manner on the periphery of the printing cylinder 22; 117 or the transfer drum 43; 44 in question. A plurality of inkjet printing units and, e.g. a blower air device 27 and/or a pressing element 28, e.g. in the form of a smoothing roller, are arranged on the periphery of each printing cylinder 22; 117 in question.

While preferred embodiments of a machine arrangement for sequential printing of sheet-type substrates, in accordance with the present invention, have been set forth fully and completely hereinabove, it will be apparent to one of skill in the art that various changes could be made without departing from the true spirit and scope of the present invention, which, is accordingly to be limited only by the appended claims.

The invention claimed is:

1. A machine arrangement for the sequential processing of sheet-format substrates, comprising a plurality of processing stations, wherein at least a first one of the processing stations includes a non-impact printing unit (06) for printing each of the substrates, wherein the first processing station that includes the non-impact printing unit (06) comprises a non-impact printing cylinder (22; 117), wherein the non-impact printing unit (06) for printing each of the substrates is arranged on the periphery of the non-impact printing cylinder (22; 117), wherein three substrates one of are and can be arranged one behind the other in a circumferential direction on a circumferential surface of the non-impact printing cylinder (22; 117), wherein a second processing station having a printed substrate dryer (123; 124) for drying the substrates that have been printed by the non-impact printing unit (06; 127) is arranged downstream of the first processing station having the non-impact printing unit (06; 127) for printing each of the substrates, in a transport direction (T) of the substrates, wherein a third processing station that includes a primer application unit (02) for priming each of the substrates and a primer application unit transport cylinder, and a fourth processing station that includes a primer dryer (07; 121) for drying the primer that has been applied to the substrates and a primer dryer transport cylinder are provided, wherein both the primer application unit (02) and the primer dryer (07; 121) are arranged upstream of the non-impact printing unit (06) in the transport direction (T) of the substrates, wherein downstream, in the transport direction (T) of the substrates, of the second processing station having the printed substrate dryer (123; 124) for drying the printed substrates, a fifth processing station having a coating unit (08) is provided, and wherein downstream of the coating unit (08), a sixth processing station having an additional dryer (09) is provided, wherein a feed unit is provided as one of a sheet feeder and a magazine feeder, wherein a feed unit transfer drum and a rocking gripper, that cooperates with the feed unit transfer drum, are provided, wherein the sheet-format substrates to be print are gripped in the feed unit and are transferred individually by the rocking gripper to the feed unit transfer drum and from there to a rotating impression cylinder and wherein the primer application unit comprises a printing couple cylinder which cooperates with the impression cylinder and which has an anilox roller which one of is and can be thrown onto the printing couple cylinder and also comprises one of at least one doctor blade which extends in an axial direction of the anilox roller and a chamber blade system.

2. The machine arrangement according to claim 1, wherein one of the primer dryer (07; 21) for drying the primer that has been applied to each of the substrates and the printed substrate dryer (123) for drying the substrates that have each been printed by the non-impact printing unit (06) and the additional dryer (09) located downstream of the coating unit (08) one is and can be embodied as a dryer for drying each of the ones of primed and printed and coated substrates using one of hot air and by irradiation with one of infrared and ultraviolet radiation.

3. The machine arrangement according to claim 2, wherein the dryer (07; 09; 121; 122; 123; 124) for drying each of the substrates by irradiation with one of infrared and ultraviolet radiation is an LED dryer.

4. The machine arrangement according to claim 1, wherein each of the substrates to be transported is held in one of a force-locking and a form-fitting manner on the circumferential surface of the non-impact printing cylinder (22; 117) by at least one retaining element.

5. The machine arrangement according to claim 1, wherein the substrates are each held in a force-locking manner by suction air on the circumferential surface of the non-impact printing cylinder (22; 117).

6. The machine arrangement according to claim 1, wherein the fifth processing station that comprises the coating unit (08) has a fifth processing station transport apparatus, wherein the fifth processing station transport apparatus has at least one fifth processing station transport cylinder.

7. The machine arrangement according to claim 6, wherein the fifth processing station transport apparatus for transporting the substrate has at least one retaining element, wherein the at least one retaining element holds each substrate in one of a force-locking and a form-fitting manner.

8. The machine arrangement according to claim 1, wherein the non-impact printing unit (06) for printing each of the substrates is embodied as at least one inkjet printing unit.

9. The machine arrangement according to claim 1, wherein at least four non-impact printing units (06; 127), each individually controlled, for printing each of the substrates are provided, wherein these at least four non-impact printing units (06; 127) are arranged one behind the other in the transport direction (T) of the substrates, wherein these at least fourth non-impact printing units (06; 127) each print with a different printing ink, wherein a designated inkjet printing unit is provided for each of these different printing inks with respect to a respective one of the at least four non-impact printing unit (06; 127).

10. The machine arrangement according to claim 1, wherein each of at least four non-impact printing unit (06; 127) for printing the substrates is configured such that it can print each of the substrates at least nearly over its entire width oriented transversely to the transport direction (T).

11. The machine arrangement according to claim 1, one of wherein the impression cylinder (119) is embodied to accommodate one of two and three substrates arranged one behind the other in a circumferential direction on a circumferential surface of the impression cylinder, and wherein each of the substrates to be transported on the circumferential surface of the impression cylinder (119) is held by at least one retaining element embodied as a gripper.

12. The machine arrangement according to claim 1, one of wherein an upstream transfer drum, (43) embodied as one of double-sized and triple-sized, is disposed immediately upstream of each printing cylinder (22; 117; 118), and wherein a downstream transfer drum (44), embodied as one of double-sized and triple-sized, is disposed immediately downstream of each printing cylinder.

13. The machine arrangement according to claim 1, wherein a last processing station, in the transport direction (T) of the substrates, is configured as a multi-pile delivery.

14. The machine arrangement according to claim 1, wherein the primer application unit (02) is configured to apply a water-based primer to the substrates.

15. The machine arrangement according to claim 1, wherein the non-impact printing unit (06) is configured to apply one of a water-based printing ink and printing ink that is cured by ultraviolet radiation to the substrates.

16. The machine arrangement according to claim 1, wherein the coating unit (08) is configured to apply one of a dispersion coating and a coating that is cured by UV radiation and a glossy coating to the substrates.

17. The machine arrangement according to claim 1, one of wherein the primer application unit (02) is configured to apply the primer over one of the full surface and a part of the surface of the substrates and wherein the coating unit (08) is configured to apply one of a full-surface coating and a partial surface coating to the substrates.

18. The machine arrangement according to claim 1, wherein the machine arrangement is configured for the manufacturing of one of folding boxes and for the production of packaging materials for one of food items and cosmetics.

19. The machine arrangement according to claim 1, wherein the machine arrangement is configured for processing substrates made of one of a single-layer and a multilayer paperboard and a cardboard, wherein substrates having a base weight of between 150 g/m2 and 600 g/m2 are classified as paperboard and substrates having a base weight of more than 600 g/m2 are classified as cardboard.

20. The machine arrangement according to claim 1, wherein the substrates have a format ranging from 340 mm×480 mm to 740 mm×1060 mm, wherein a first number in the format specification indicates a length in the transport direction (T) of the substrates and a second number in the format specification indicates a width of the substrates orthogonally to the transport direction (T).

* * * * *